US011737967B2

(12) United States Patent
Schumacher et al.

(10) Patent No.: US 11,737,967 B2
(45) Date of Patent: Aug. 29, 2023

(54) INCREASING THE STABILITY OF AGENTS FOR TREATING KERATIN MATERIAL

(71) Applicant: Henkel AG & Co. KGaA, Duesseldorf (DE)

(72) Inventors: Ulrike Schumacher, Duesseldorf (DE); Juergen Schoepgens, Schwalmtal (DE); Marc Nowottny, Moenchengladbach (DE); Caroline Kriener, Duesseldorf (DE); Claudia Kolonko, Remscheid (DE); Phillip Jaiser, Langenfeld (DE); Carsten Mathiaszyk, Essen (DE); Torsten Lechner, Langenfeld (DE); Gabriele Weser, Neuss (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/614,049

(22) PCT Filed: Mar. 30, 2020

(86) PCT No.: PCT/EP2020/058933
§ 371 (c)(1),
(2) Date: Nov. 24, 2021

(87) PCT Pub. No.: WO2020/239291
PCT Pub. Date: Dec. 3, 2020

(65) Prior Publication Data
US 2022/0233423 A1 Jul. 28, 2022

(30) Foreign Application Priority Data
May 29, 2019 (DE) .......................... 102019207896.6

(51) Int. Cl.
A61Q 5/10 (2006.01)
A61K 8/58 (2006.01)
A61K 8/06 (2006.01)
A61K 8/34 (2006.01)
A61K 8/73 (2006.01)
A61K 8/81 (2006.01)
A61K 8/86 (2006.01)

(52) U.S. Cl.
CPC .............. A61K 8/585 (2013.01); A61K 8/062 (2013.01); A61K 8/342 (2013.01); A61K 8/731 (2013.01); A61K 8/8147 (2013.01); A61K 8/86 (2013.01); A61Q 5/10 (2013.01); A61K 2800/882 (2013.01); A61K 2800/884 (2013.01); A61K 2800/95 (2013.01)

(58) Field of Classification Search
CPC ........ A61K 8/585; A61K 8/062; A61K 8/342; A61K 8/731; A61K 8/8147; A61K 8/86; A61K 2800/882; A61K 2800/884; A61K 2800/95; A61K 2800/31; A61Q 5/10; A61Q 5/065
USPC .......................................................... 8/405
See application file for complete search history.

(56) References Cited

U.S. PATENT DOCUMENTS

2005/0214236 A1 9/2005 Peng et al.
2010/0083446 A1* 4/2010 Brun ...................... A61K 8/891
8/405
2010/0297049 A1 11/2010 Samain et al.

FOREIGN PATENT DOCUMENTS

| EP | 2168633 | A2 | 3/2010 | | |
| FR | 2936413 | A1 * | 4/2010 | ............... | A61Q 5/02 |
| FR | 2936414 | A1 * | 4/2010 | ............... | A61Q 5/10 |
| FR | 2964869 | A1 * | 3/2012 | ............... | A61K 8/89 |
| WO | 2013068979 | A2 | 5/2013 | | |

* cited by examiner

Primary Examiner — Eisa B Elhilo
(74) Attorney, Agent, or Firm — Lorenz & Kopf, LLP

(57) ABSTRACT

It is an object of the present disclosure to provide a method for the preparation and use of an agent for coloring keratinous material, in particular human hair, comprising the following steps:
(1) Preparation of a first composition (A) comprising
  (A1) less than about 10% by weight of water and
  (A2) one or more organic $C_1$-$C_6$ alkoxy silanes and/or condensation products thereof, and
(2) Preparation of a second composition (B) containing
  (B1) Water and
  (B2) one or more fat components and
  (B3) one or more colorant compounds selected from the group of pigments and/or direct dyes,
(3) Storage of the composition (A) and/or (B) for a period of at least about 24 hours,
(4) mixing compositions (A) and (B),
(5) Application of the mixture of (A) and (B) on the keratinic material.

20 Claims, No Drawings

INCREASING THE STABILITY OF AGENTS FOR TREATING KERATIN MATERIAL

CROSS-REFERENCE TO RELATED APPLICATION

This application is a U.S. National-Stage entry under 35 U.S.C. § 371 based on International Application No. PCT/EP2020/058933, filed Mar. 30, 2020, which was published under PCT Article 21(2) and which claims priority to German Application No. 102019207896.6, filed May 29, 2019, which are all hereby incorporated in their entirety by reference.

TECHNICAL FIELD

The present application is in the field of cosmetics and relates to a method for the treatment of keratinic material, in particular human hair, which comprises the use of two compositions (A) and (B). Composition (A) is a low-water preparation containing at least one organic $C_1$-$C_6$ alkoxysilane, and composition (B) contains, in addition to water, at least one fatty constituent and at least one coloring compound. The process as contemplated herein is exemplified by the preparation of the preparations (A) and (B), their storage for a certain minimum period, their mixing and the application of this mixture to the keratin material.

A second object of the present disclosure is a ready-to-use composition for dyeing keratinous material, which is prepared by preparing, storing and mixing the two previously described compositions (A) and (B).

A third object of the present disclosure is a kit-of-parts for dyeing keratinous material, which comprises, separately packaged in two packaging units, the two compositions (A) and (B) described above

BACKGROUND

The change in shape and color of keratin fibers, especially hair, is an important area of modern cosmetics. To change the hair color, the expert knows various coloring systems depending on coloring requirements. Oxidation dyes are usually used for permanent, intensive dyeing's with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

BRIEF SUMMARY

Methods for coloring keratinous material and a kit-of-parts for the same are provided. In an exemplary embodiment, the method for coloring keratinous material includes preparing a first composition (A) that includes less than about 10% water and a $C_1$-$C_6$ alkoxy silane and/or a condensation product of the same. A second composition (B) is prepared, and includes water, one or more fat components, and a colorant selected from the group of pigments and/or direct dyes. The first and second compositions (A) and (B) are stored for at least about 24 hours, and then mixed together. The mixed compositions (A) and (B) are then applied to the keratinous material.

In another embodiment, a kit-of-parts for coloring keratinous material is provided. The kit-of-parts includes a first container containing a first composition (A) and a second container containing a second composition (B). The first composition (A) includes (A1) less than about 10% by weight of water and (A2) one or more organic $C_1$-$C_6$ alkoxy silanes and/or condensation products thereof. The second composition (B) includes (B1) water, (B2) one or more fat components, and (B3) one or more colorant compounds selected from the group of pigments and/or direct dyes.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

EP 2168633 B1 deals with the task of producing long-lasting hair colorations using pigments. The paper teaches that when a combination of pigment, organic silicon compound, hydrophobic polymer and a solvent is used on hair, it is possible to produce colorations that are particularly resistant to shampooing.

The organic silicon compounds used in EP 2168633 B1 are reactive compounds from the class of alkoxy silanes. These alkoxy silanes hydrolyze at high rates in the presence of water and form hydrolysis products and/or condensation products, depending on the amounts of alkoxy silane and water used in each case. The influence of the amount of water used in this reaction on the properties of the hydrolysis or condensation product are described, for example, in WO 2013068979 A2.

When these alkoxy silanes or their hydrolysis or condensation products are applied to keratinous material, a film or coating forms on the keratinous material, which completely coats the keratinous material and, in this way, strongly influences the properties of the keratinous material. Possible areas of application include permanent styling or permanent shape modification of keratin fibers. In this process, the keratin fibers are mechanically shaped into the desired form and then fixed in this form by forming the coating described above. Another particularly suitable application is the coloring of keratin material; in this application, the coating or film is produced in the presence of a coloring compound, for example a pigment. The film colored by the pigment remains on the keratin material or keratin fibers and results in surprisingly wash-resistant colorations.

The great advantage of the alkoxy silane-based dyeing principle is that the high reactivity of this class of compounds enables very fast coating. This means that extremely good coloring results can be achieved after very short application periods of just a few minutes. In addition to these advantages, however, the high reactivity of alkoxy silanes also has some disadvantages.

Due to their high reactivity, the organic alkoxy silanes cannot be prepared together with larger amounts of water, as a large excess of water initiates immediate hydrolysis and subsequent polymerization. The polymerization that takes place during storage of the alkoxy silanes in aqueous medium manifests itself in a thickening or gelation of the aqueous preparation. This makes the preparations so highly viscous, gelatinous or gel-like that they can no longer be applied evenly to the keratin material. In addition, storage of the alkoxy silanes in the presence of high amounts of water is associated with a loss of their reactivity, so that the formation of a resistant coating on the keratin material is also no longer possible.

For these reasons, it is necessary to store the organic alkoxy silanes in a water-free or water-poor environment and to prepare the corresponding preparations in a separate container. Due to their high reactivity, alkoxy silanes can react not only with water but also with other cosmetic ingredients. To avoid all undesirable reactions, the preparations with alkoxy silanes therefore preferably do not contain any other ingredients or only the selected ingredients that have been found to be chemically inert towards the alkoxy silanes. Accordingly, the concentration of the alkoxy silanes in the preparation is preferably chosen to be relatively high. The low-water preparations containing the alkoxy silanes in relatively high concentrations can also be referred to as "silane blends."

For application to the keratin material, the user must now convert this relatively highly concentrated silane blend into a ready-to-use mixture. In this ready-to-use mixture, on the one hand the concentration of organic alkoxy silanes is reduced, and on the other hand the application mixture also contains a higher proportion of water (or an alternative protic ingredient), which triggers the polymerization leading to the coating.

It has proved extremely challenging to optimally adapt the polymerization rate, i.e., the speed at which the coating forms on the keratin material, to the application conditions.

When applied to human hair, for example, a polymerization rate that is too fast will result in polymerization being completed before all hair sections have been treated. Too rapid polymerization therefore makes whole-head treatment impossible. In the coloring process, the excessively fast polymerization manifests itself in an extremely uneven color result, so that the hair sections that were treated last are only poorly colored.

On the other hand, if polymerization is too slow, all areas of the hair can be treated without time pressure, but this increases the application time. Therefore, if polymerization is too slow, the great advantage of this dyeing technology, the formation of washfast dyeing's within shortest application periods, does not come into effect.

A central task of the present application was to find a process for treating keratinous material by which the polymerization rate of organic alkoxy silanes could be adapted to the conditions of use, to the conditions prevailing when applied to the human head. In other words, a process was sought by which the organic alkoxy silanes would remain reactive long enough to allow whole-head treatment without unduly extending the application period.

In initial series of experiments, it has surprisingly been found that this task can be solved very well if the keratin material is treated in a process in which two compositions (A) and (B) are applied to the keratin material. The first composition (A) is the low water silane blend described previously. The second composition (B) is a water-containing emulsion and contains at least one coloring compound in addition to a fatty component. If the two compositions (A) and (B) are mixed and applied to the keratinous material in this mixture, the reactivity of the silane blend could be optimally adapted to the application conditions prevailing in a whole-head hair dyeing process. Even more complicated or time-consuming dyeing techniques, such as the dyeing of highlights specially arranged on the head, could be realized using the process as contemplated herein, so that dyeing's with a particularly high degree of uniformity could be produced in this way.

Further tests have shown that the method described above has one disadvantage in addition to its advantages. Thus, it has been shown that the use of the silane blend (A) in combination with an emulsion-like composition (B) can again lead to dyeing results with deteriorated fastness to washing compared to the use of a gel-like composition (B).

The second essential task of the present disclosure was therefore to provide a dyeing system based on organic alkoxy silanes, the reactivity of which is optimally adapted to the conditions prevailing during dyeing, without sacrificing any of its fastness properties, in particular its fastness to washing. Optimally, this dyeing system should have both optimum reactivity and improved wash fastness.

In a manner not foreseeable by the skilled person, it has now been found that the wash fastness of the dyeing's obtained with the application of the two compositions (A) and (B) could be significantly improved if at least one of the compositions (A) and/or (B) underwent a certain storage time or also maturing time before their application on the keratin material.

A first object of the present disclosure is a method for preparing and using an agent for coloring keratinous material, in particular human hair, comprising the following steps:

(1) Preparation of a first composition (A) comprising
   (A1) less than about 10% by weight of water and
   (A2) one or more organic $C_1$-$C_6$ alkoxy silanes and/or condensation products thereof, and
(2) Preparation of a second composition (B) comprising
   (B1) Water and
   (B2) one or more fat components and
   (B3) one or more colorant compounds selected from the group of pigments and/or direct dyes,
(3) Storage of the composition (A) and/or (B) for a period of at least about 24 hours,
(4) mixing compositions (A) and (B),
(5) Application of the mixture of (A) and (B) on the keratinic material.

Surprisingly, the reactivity of the organic $C_1$-$C_6$ Alkoxysilanes (A2) can be optimally adapted to the application conditions prevailing in a full-head hair coloring process. Even more complicated or time-consuming dyeing techniques, such as the dyeing of highlights specially arranged on the head, could be realized using the process as contemplated herein. When both compositions (A) and (B) were used in the above-mentioned dyeing process, dyeing's with a particularly high degree of uniformity could be produced in this way on keratin material, especially on human hair.

Surprisingly, the dyeing's produced in this way were also exemplified by very good wash fastness.

Coloring of Keratinic Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Agents for treating keratinous material are understood to mean, for example, features for coloring the keratinous material, features for reshaping or shaping keratinous material, in particular keratinous fibers, or also features for conditioning or caring for the keratinous material. The agents prepared by the process of the present disclosure are particularly suitable for coloring keratinous material, in particular keratinous fibers, which are preferably human hair.

The term "coloring agent" is used in the context of the present disclosure to refer to a coloring of the keratin material, of the hair, caused using coloring compounds, such as pigments, mica, direct dyes and/or thermochromic and photochromic dyes. In this staining process, the colorant compounds are deposited in a particularly homogeneous and smooth film on the surface of the keratin material or diffuse into the keratin fiber. The film forms in situ by oligomerization or polymerization of the organic alkoxy silane(s), and by the interaction of the color-imparting compound and organic silicon compound and optionally other ingredients, such as a film-forming, polymer.

Composition (A)

Step (1) of the process as contemplated herein is exemplified by the preparation of the first composition (A). The composition (A) contains less than about 10% by weight of water (A1) and one or more organic $C_1$-$C_6$ alkoxy silanes and/or their condensation products (A2).

Water Content (A1) in the Composition (A)

To ensure sufficiently high storage stability, composition (A) is exemplified by being low in water, preferably substantially free of water. Therefore, the composition (A) contains—based on the total weight of the composition (A)—less than about 10% by weight of water.

At a water content of just below about 10% by weight, the compositions (A) are stable in storage over longer periods. However, to further improve the storage stability and to ensure a sufficiently high reactivity of the organic $C_1$-$C_6$ alkoxy silanes (A2), it has been found to be particularly preferable to further lower the water content in the composition (A). For this reason, first composition (A)—based on the total weight of composition (A)—preferably contains about 0.01 to about 9.5% by weight, further preferably about 0.01 to about 8.0% by weight, still further preferably about 0.01 to about 6.0 and very particularly preferably about 0.01 to about 4.0% by weight of water (A1).

In a very particularly preferred embodiment, a process as contemplated herein is exemplified in that the first composition (A) contains—based on the total weight of the composition (A)—about 0.01 to about 9.5% by weight, preferably about 0.01 to about 8.0% by weight, further preferably about 0.01 to about 6.0 and very particularly preferably about 0.01 to about 4.0% by weight of water (A1).

Organic $C_1$-$C_6$ Alkoxy Silanes (A2) and/or their Condensation Products in the Composition (A)

As a second ingredient essential to the present disclosure, the composition (A) contains one or more organic $C_1$-$C_6$ alkoxy silanes (A2) and/or their condensation products.

The organic $C_1$-$C_6$ alkoxy silane(s) are organic, non-polymeric silicon compounds, preferably selected from the group of silanes containing one, two or three silicon Organic silicon compounds, alternatively called organo-silicon compounds, are compounds which either have a direct silicon-carbon bond (Si—C) or in which the carbon is bonded to the silicon atom via an oxygen, nitrogen or sulfur atom. The organic silicon compounds of the present disclosure are preferably compounds containing one to three silicon atoms. Organic silicon compounds preferably contain one or two silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups.

A feature of the $C_1$-$C_6$ alkoxy silanes of the present disclosure is that at least one $C_1$-$C_6$ alkoxy group is directly bonded to a silicon atom. The $C_1$-$C_6$ alkoxy silanes as contemplated herein thus comprise at least one structural unit R'R''R'''Si—O—($C_1$-$C_6$ alkyl) where the radicals R', R'' and R''' stand for the three remaining bond valencies of the silicon atom.

The $C_1$-$C_6$ alkoxy group or groups bonded to the silicon atom are very reactive and are hydrolyzed at high rates in the presence of water, the reaction rate depending, among other things, on the number of hydrolysable groups per molecule. If the hydrolysable $C_1$-$C_6$ alkoxy group is an ethoxy group, the organic silicon compound preferably contains a structural unit R'R''R'''Si—O—CH2-CH3. The R', R'' and R''' residues again represent the three remaining free valences of the silicon atom.

Even the addition of small amounts of water leads first to hydrolysis and then to a condensation reaction between the organic alkoxy silanes. For this reason, both the organic alkoxy silanes (A2) and their condensation products may be present in the composition.

A condensation product is understood to be a product formed by reaction of at least two organic $C_1$-$C_6$ alkoxy silanes with elimination of water and/or with elimination of a $C_1$-$C_6$ alkanol.

The condensation products can, for example, be dimers, or even trimers or oligomers, where in the condensation products are always in balance with the monomers.

Depending on the amount of water used or consumed in the hydrolysis, the equilibrium shifts from monomeric $C_1$-$C_6$ alkoxysilane to condensation product.

In a very particularly preferred embodiment, a process as contemplated herein is exemplified in that the composition (A) comprises one or more organic $C_1$-$C_6$ alkoxy silanes (A2) selected from silanes having one, two or three silicon atoms, the organic silicon compound further comprising one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A very particularly preferred method as contemplated herein is exemplified in that the composition (A) comprises one or more organic $C_1$-$C_6$ alkoxy silanes (A2) selected from the group of silanes having one, two or three silicon atoms, and wherein the $C_1$-$C_6$ alkoxy silanes further comprise one or more basic chemical functions.

Particularly good results were obtained when $C_1$-$C_6$ alkoxy silanes of the formula (S-I) and/or (S-II) were used in the process as contemplated herein. Since, as previously described, hydrolysis/condensation already starts at traces of moisture, the condensation products of the $C_1$-$C_6$ alkoxy silanes of formula (S-I) and/or (S-II) are also included in this embodiment.

In another very particularly preferred embodiment, a process as contemplated herein is exemplified in that the first composition (A) comprises one or more organic $C_1$-$C_6$ alkoxy silanes (A2) of the formula (S-I) and/or (S-II), $$R_1R_2N\text{-}L\text{-}Si(OR_3)_a(R_4)_b \qquad (S4)$$

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a, stands for an integer from 1 to 3, and
b stands for the integer 3-a, and $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \qquad (S\text{-}II)$$

where
R5, R5', R5", R6, R6' and R6" independently represent a $C_1$-$C_6$ alkyl group,
A, A', A", A''' and A'''' independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III), $$(A'''')\text{-}Si(R_6'')_{d''}(OR_5'')_{c''} \qquad (S\text{-}III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g and h is different from 0, and/or their condensation products.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A''' and A'''' in the compounds of formula (S-I) and (S-II) are explained below as examples: Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In the organic silicon compounds of the formula (S-I)

$$R_1R_2N\text{-}L\text{-}Si(OR_3)_a(R_4)_b \qquad (S4),$$

the radicals $R_1$ and $R_2$ independently of one another represent a hydrogen atom or a $C_1$-$C_6$ alkyl group. Very preferably, $R_1$ and $R_2$ both represent a hydrogen atom.

In the middle part of the organic silicon compound is the structural unit or the linker -L- which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each -L grouping may form—two bonds.

Preferably -L- stands for a linear, divalent $C_1$-$C_{20}$ alkylene group. Further preferably -L- stands for a linear divalent $C_1$-$C_6$ alkylene group. Particularly preferred -L stands for a methylene group ($CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The organic silicon compounds of formula (S-I) as contemplated herein.

$$R_1R_2N\text{-}L\text{-}Si(OR_3)_a(R_4)_b \qquad (S\text{-}I),$$

one end of each carries the silicon-containing group —Si$(OR_3)_a(R_4)_b$.

In the terminal structural unit —Si$(OR_3)_a(R_4)_b$ $R_3$ and $R_4$ independently represent a $C_1$-$C_6$ alkyl group, and particularly preferably $R_3$ and $R_4$ independently represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Keratin treatment agents with particularly good properties could be prepared if the composition (A) contains at least one organic $C_1$-$C_6$ alkoxy silane of the formula (S-I) in which the radicals $R_3$, $R_4$ independently of one another represent a methyl group or an ethyl group.

Furthermore, dyeing's with the best wash fastnesses could be obtained if the composition (A) comprises at least one organic $C_1$-$C_6$ alkoxy silane of the formula (S-I) in which the radical a represents the number 3. In this case the rest b stands for the number 0.

In a further preferred embodiment, a process as contemplated herein is exemplified in that the composition (A) comprises one or more organic $C_1$-$C_6$ alkoxy silanes of the formula (S-I),
where
$R_3$, $R_4$ independently of one another represent a methyl group or an ethyl group and
a stands for the number 3 and
b stands for the number 0.

In a further preferred embodiment, a process as contemplated herein is exemplified in that the composition (A) comprises at least one or more organic $C_1$-$C_6$ alkoxy silanes of the formula (S-I), $$R_1R_2N\text{-}L\text{-}Si(OR_3)_a(R_4)_b \qquad (S\text{-}I),$$

where
$R_1$, $R_2$ both represent a hydrogen atom, and
L represents a linear, divalent $C_1$-$C_6$-alkylene group, preferably a propylene group (—$CH_2$—$CH_2$—$CH_2$—) or an ethylene group (—$CH_2$—$CH_2$—),
$R_3$ represents an ethyl group or a methyl group,
$R_4$ represents a methyl group or an ethyl group, a stands for the number 3 and
b stands for the number 0.

Organic silicon compounds of the formula (I) which are particularly suitable for solving the problem as contemplated herein are

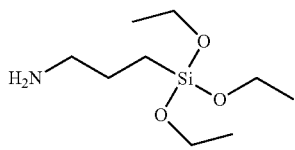

-(3-Aminopropyl)triethoxysilane

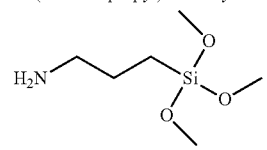

-(3-Aminopropyl)trimethoxysilane

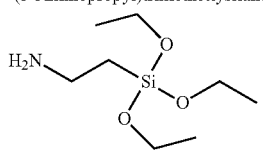

-(2-Aminoethyl)triethoxysilane

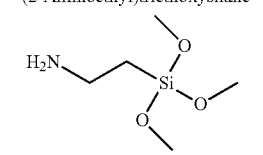

-(2-Aminoethyl)trimethoxysilane

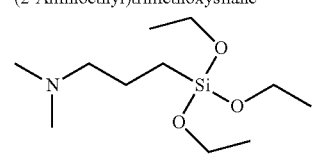

-(3-Dimethylaminopropyl)triethoxysilane

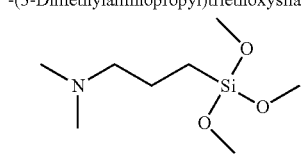

-(3-Dimethylaminopropyl)trimethoxysilane

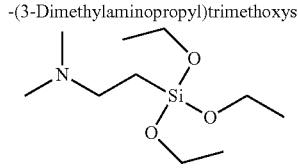

-(2-Dimethylaminoethyl)triethoxysilane.

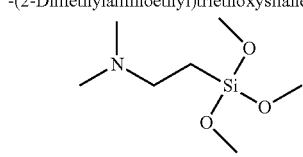

-(2-Dimethylaminoethyl)trimethoxysilane and/or

In a further preferred embodiment, a process as contemplated herein is exemplified in that the first composition (A) comprises at least one organic $C_1$-$C_6$ alkoxysilane (A2) of formula (S-I) selected from the group of (3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane,
(2-Dimethylaminoethyl)trimethoxysilane and/or their condensation products.

The organic silicon compound of formula (I) is commercially available. (3-aminopropyl)trimethoxysilane, for example, can be purchased from Sigma-Aldrich®. Also (3-aminopropyl)triethoxysilane is commercially available from Sigma-Aldrich®.

In a further embodiment of the process as contemplated herein, composition (A) may also comprise one or more organic $C_1$-$C_6$ alkoxy silanes of formula (S-II), $$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad \text{(S-II)}.$$

The organosilicon compounds of the formula (S-II) as contemplated herein each carry at their two ends the silicon-containing groupings $(R_5O)_c(R_6)_dSi$— and —$Si(R_6')_{d'}(OR_5')_{c'}$.

In the central part of the molecule of formula (S-II) there are the groups -$(A)_e$- and —$[NR_7\text{-}(A')]_f$- and —$[O\text{-}(A'')]_g$- and —$[NR_8\text{-}(A''')]_h$-. Here, each of the radicals e, f, g and h can independently of one another stand for the number 0 or 1, with the proviso that at least one of the radicals e, f, g and h is different from 0. In other words, an organic silicon compound of formula (II) as contemplated herein contains at least one grouping from the group of -(A)- and —[NR$_7$-(A')]- and —[O-(A'')]- and —[NR$_8$-(A''')]-.

In the two terminal structural units $(R_5O)_c(R_6)_dSi$— and —$Si(R_6')_{d'}(OR_5')_{c'}$, the residues R5, R5', R5" independently represent a $C_1$-$C_6$ alkyl group. The radicals R6, R6' and R6" independently represent a $C_1$-$C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In a further preferred embodiment, a process as contemplated herein is exemplified in that the composition (A) comprises one or more organic $C_1$-$C_6$ alkoxy silanes of the formula (S-II), $$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad \text{(S-II)},$$

where
$R_5$ and $R_5'$ independently represent a methyl group or an ethyl group,
c and c' both stand for the number 3 and
d and d' both stand for the number 0.

When c and c' are both 3 and d and d' are both 0, the organic silicon compounds as contemplated herein correspond to the formula (S-IIa)

$$(R_5O)_3Si\text{-}(A)_e\text{-}[NR_7\text{-}(A')]_f\text{—}[O\text{-}(A''')]_g\text{—}[NR_8\text{-}(A''')]_h\text{—}Si(OR_5')_3 \quad \text{(S-IIa)}.$$

The radicals e, f, g and h can independently stand for the number 0 or 1, whereby at least one radical from e, f, g and h is different from zero. The abbreviations e, f, g and h thus define which of the groupings -(A)$_e$- and —[NR$_7$-(A')]$_f$- and —[O-(A")]$_g$- and —[NR$_8$-(A''')]$_h$- are in the middle part of the organic silicon compound of formula (II).

In this context, the presence of certain groupings has proven to be particularly advantageous in terms of achieving washfast dyeing results. Particularly good results could be obtained if at least two of the residues e, f, g and h stand for the number 1. Especially preferred e and f both stand for the number 1. Furthermore, g and h both stand for the number 0.

When e and f are both 1 and g and h are both 0, the organic silicon compounds as contemplated herein are represented by the formula (S-IIb)

(R$_5$O)$_c$(R$_6$)$_d$Si-(A)-[NR$_7$-(A')]—Si(R$_6'$)$_{d'}$(OR$_5'$)$_{c'}$. (S-IIb).

The radicals A, A', A'', A''' and A'''' independently represent a linear or branched divalent C$_1$-C$_{20}$ alkylene group. Preferably the radicals A, A', A'', A''' and A'''' independently of one another represent a linear, divalent C$_1$-C$_{20}$ alkylene group. Further preferably the radicals A, A', A'', A''' and A'''' independently represent a linear divalent C$_1$-C$_6$ alkylene group.

The divalent C$_1$-C$_{20}$ alkylene group may alternatively be referred to as a divalent or divalent C$_1$-C$_{20}$ alkylene group, by which is meant that each grouping A, A', A'', A''' and A'''' may form two bonds.

In particular, the radicals A, A', A'', A''' and A'''' independently of one another represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Very preferably, the radicals A, A', A'', A''' and A'''' represent a propylene group (—CH$_2$—CH$_2$—CH$_2$—).

If the radical f represents the number 1, then the organic silicon compound of formula (II) as contemplated herein contains a structural grouping —[NR$_7$-(A')]-. If the radical f represents the number 1, then the organic silicon compound of formula (II) as contemplated herein contains a structural grouping —[NR$_8$-(A''')]-.

Wherein R$_7$ and R$_8$ independently represent a hydrogen atom, a C$_1$-C$_6$ alkyl group, a hydroxy-C$_1$-C$_6$ alkyl group, a C$_2$-C$_6$ alkenyl group, an amino-C$_1$-C$_6$ alkyl group or a group of the formula (S-III)

-(A'''')-Si(R$_6''$)$_{d''}$(OR$_5''$)$_{c''}$ (S-III).

Very preferably the radicals R7 and R8 independently of one another represent a hydrogen atom, a methyl group, a 2-hydroxyethyl group, a 2-alkenyl group, a 2-aminoethyl group or a grouping of the formula (S-III).

If the radical f represents the number 1 and the radical h represents the number 0, the organic silicon compound as contemplated herein contains the grouping [NR$_7$-(A')] but not the grouping —[NR$_8$-(A''')] If the radical R$_7$ now stands for a grouping of the formula (III), the organic silicone compound comprises 3 reactive silane groups.

In a further preferred embodiment, a process as contemplated herein is exemplified in that the composition (A) comprises one or more organic C$_1$-C$_6$ alkoxy silanes (A2) of the formula (S-II), (R$_5$O)$_c$(R$_6$)$_d$Si-(A)$_e$-[NR$_7$-(A')]$_f$—[O-(A")]$_g$—[NR$_8$-(A''')]$_h$—Si(R$_6'$)$_{d'}$(R$_5'$)$_{c'}$ (II), where
e and f both stand for the number 1,
g and h both stand for the number 0, A and A' independently represent a linear, divalent C$_1$-C$_6$ alkylene group and R$_7$ represents a hydrogen atom, a methyl group, a 2-hydroxyethyl group, a 2-alkenyl group, a 2-aminoethyl group or a group of formula (S-III).

In a further preferred embodiment, a process as contemplated herein is exemplified in that the composition (A) comprises one or more organic C$_1$-C$_6$ alkoxy silanes (A2) of the formula (S-II), where e and f both stand for the number 1, g and h both stand for the number 0, A and A' independently of one another represent a methylene group (—CH$_2$—), an ethylene group (—CH$_2$—CH$_2$—) or a propylene group (—CH$_2$—CH$_2$—CH$_2$—), and R$_7$ represents a hydrogen atom, a methyl group, a 2-hydroxyethyl group, a 2-alkenyl group, a 2-aminoethyl group or a group of formula (S-III).

Organic silicon compounds of the formula (S-II) which are well suited for solving the problem as contemplated herein are

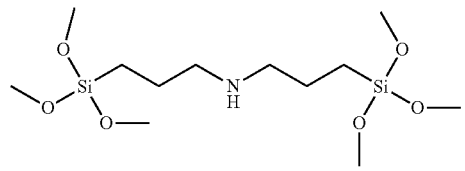

-3-(Trimethoxysilyl)-N-[3-(trimethoxysilyl)propyl]-1-propanamine

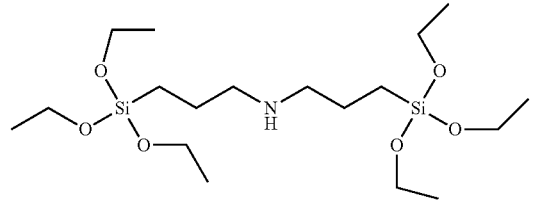

-3-(Triethoxysilyl)-N-[3-(triethoxysilyl)propyl]-1-propanamine

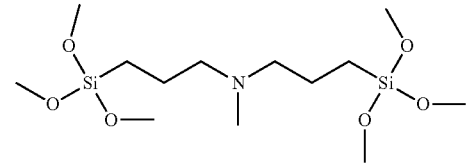

-N-methyl-3-(trimethoxysilyl)-N-[3-(trimethoxysilyl)propyl]-1-propanamine

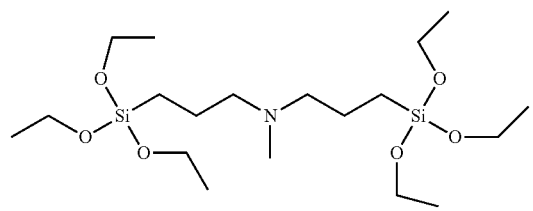

-N-Methyl-3-(triethoxysilyl)-N-[3-(triethoxysilyl)propyl]-1-propanamine

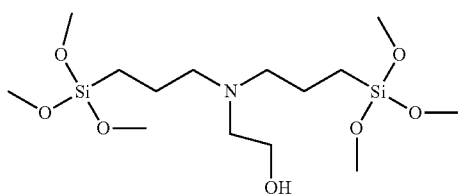

-2-[Bis[3-(trimethoxysilyl)propyl]amino]-ethanol

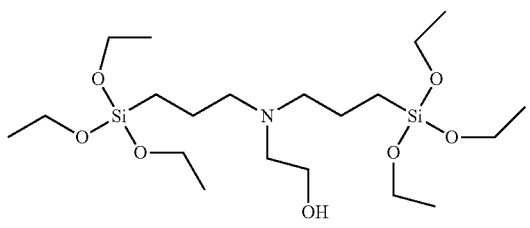

-2-[Bis[3-(triethoxysilyl)propyl]amino]ethanol

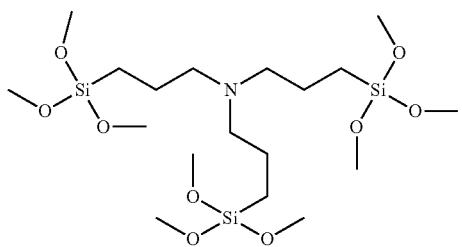

-3-(Trimethoxysilyl)-N,N-bis[3-(trimethoxysilyl)propyl]-1-propanamine

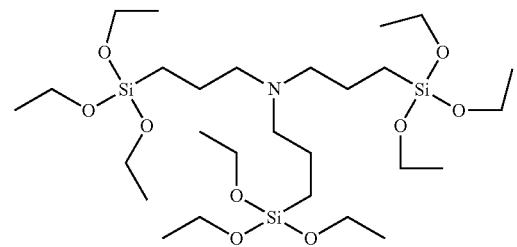

-3-(Triethoxysilyl)-N,N-bis[3-(triethoxysilyl)propyl]-1-propanamine

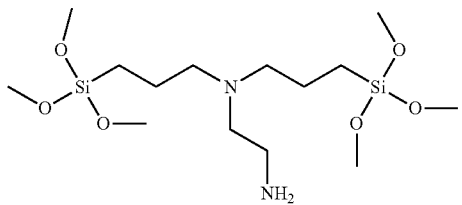

-N1,N1-Bis[3-(trimethoxysilyl)propyl]-1,2-ethanediamine,

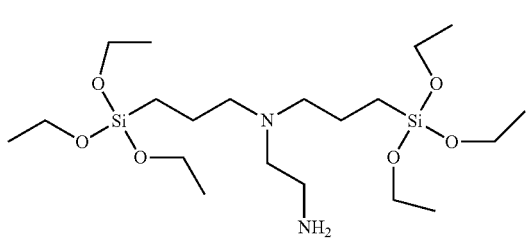

-N1,N1-Bis[3-(triethoxysilyl)propyl]-1,2-ethanediamine,

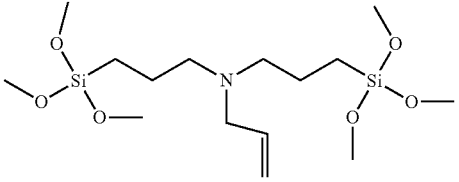

-N,N-Bis[3-(trimethoxysilyl)propyl]-2-propene-1-amine

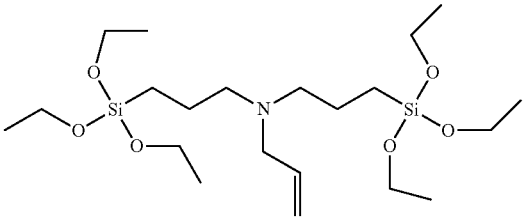

-N,N-Bis[3-(triethoxysilyl)propyl]-2-propene-1-amine

The organic silicon compounds of formula (S-II) are commercially available.

Bis(trimethoxysilylpropyl)amines with the CAS number 82985-35-1 can be purchased from Sigma-Aldrich®.

Bis[3-(triethoxysilyl)propyl]amines with the CAS number 13497-18-2 can be purchased from Sigma-Aldrich®, for example.

N-methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich® or Fluorochem®.

3-(triethoxysilyl)-N,N-bis[3-(triethoxysilyl)propyl]-1-propanamine with the CAS number 18784-74-2 can be purchased for example from Fluorochem® or Sigma-Aldrich®.

In a further preferred embodiment, a process as contemplated herein is exemplified in that the composition (A) comprises one or more organic $C_1$-$C_6$ alkoxy silanes of formula (S-II) selected from the group of 3-(Trimethoxysilyl)-N-[3-(trimethoxysilyl)propyl]-1-propanamine
3-(Triethoxysilyl)-N-[3-(triethoxysilyl) propyl]-1-propanamine
N-Methyl-3-(trimethoxysilyl)-N-[3-(trimethoxysilyl) propyl]-1-propanamine
N-Methyl-3-(triethoxysilyl)-N-[3-(triethoxysilyl) propyl]-1-propanamine
2-[Bis[3-(trimethoxysilyl) propyl]amino]-ethanol
2-[Bis[3-(triethoxysilyl) propyl]amino]ethanol
3-(Trimethoxysilyl)-N,N-bis[3-(trimethoxysilyl) propyl]-1-propanamine
3-(Triethoxysilyl)-N,N-bis[3-(triethoxysilyl) propyl]-1-propanamine
N1,N1-Bis[3-(trimethoxysilyl) propyl]-1,2-ethanediamine,
N1,N1-Bis[3-(triethoxysilyl) propyl]-1,2-ethanediamine,
N,N-Bis[3-(trimethoxysilyl)propyl]-2-Propen-1-amine and/or
N,N-Bis[3-(triethoxysilyl)propyl]-2-propen-1-amine, and/or their condensation products.

In further dyeing trials, it has also been found to be particularly advantageous if at least one organic $C_1$-$C_6$ alkoxy silane (A2) of the formula (S-IV) was used in the process as contemplated herein $$R_9Si(OR_{10})_k(R_{11})_m \qquad \text{(S-IV)}.$$

The compounds of formula (S-IV) are organic silicon compounds selected from silanes having one, two or three silicon atoms, wherein the organic silicon compound comprises one or more hydrolysable groups per molecule.

The organic silicon compound(s) of formula (S-IV) may also be referred to as silanes of the alkyl-$C_1$-$C_6$-alkoxysilane type, $$R_9Si(OR_{10})_k(R_{11})_m \quad (S\text{-}IV),$$

where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group
k is an integer from 1 to 3, and
m stands for the integer 3-k.

In a further embodiment, a particularly preferred method as contemplated herein is exemplified in that the first composition (A) contains one or more organic $C_1$-$C_6$ alkoxy silanes (A2) of the formula (S-IV), $$R_9Si(OR_{10})_k(R_{11})_m \quad (S\text{-}IV),$$

where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group
k is an integer from 1 to 3, and
m stands for the integer 3-k, and/or their condensation products.

In the organic $C_1$-$C_6$ alkoxy silanes of formula (S-IV), the $R_9$ radical represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, $R_9$ stands for a methyl group, an ethyl group or an n-octyl group.

In the organic silicon compounds of formula (S-IV), the radical $R_{10}$ represents a $C_1$-$C_6$ alkyl group. Highly preferred $R_{10}$ stands for a methyl group or an ethyl group.

In the organic silicon compounds of formula (S-IV), the radical $R_{11}$ represents a $C_1$-$C_6$ alkyl group. Highly preferred $R_{11}$ stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyeing's with the best wash fastnesses could be obtained when the composition (A) contains at least one organic $C_1$-$C_6$ alkoxy silane (A2) of formula (S-IV) in which the radical k represents the number 3. In this case the rest m stands for the number 0.

Organic silicon compounds of the formula (S-IV) which are particularly suitable for solving the problem as contemplated herein are

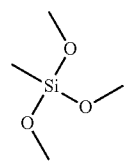
-Methyltrimethoxysilane

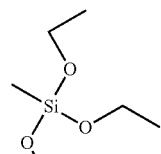
-Methyltriethoxysilane

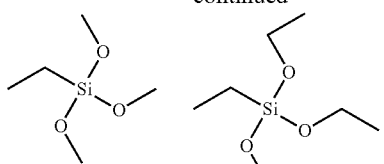
-Ethyltrimethoxysilane   -Ethyltriethoxysilane

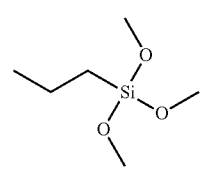 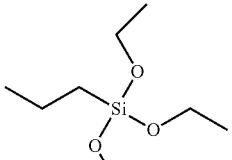
-n-Propyltrimethoxysilane
(also known as propyltrimethoxysilane)   -n-Propyltriethoxysilane
(also known as propyltriethoxysilane)

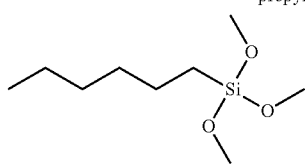
-n-Hexyltrimethoxysilane (also known as hexyltrimethoxysilane)

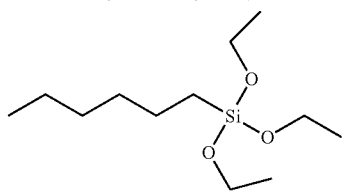
-n-Hexyltriethoxysilane (also known as hexyltriethoxysilane)

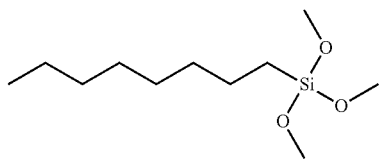
-n-Octyltrimethoxysilane (also known as octyltrimethoxysilane)

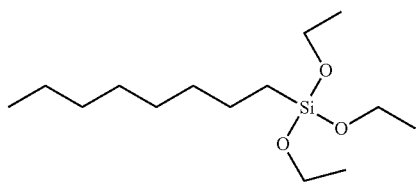
-n-Octyltriethoxysilane (also known as octyltriethoxysilane)

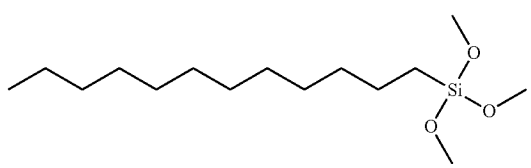
-n-Dodecyltrimethoxysilane (also known as dodecyltrimethoxysilane) and/or -continued

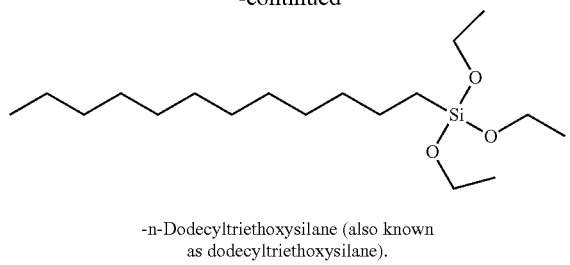

n-Dodecyltriethoxysilane (also known as dodecyltriethoxysilane).

In a further preferred embodiment, a process as contemplated herein is exemplified in that the first composition (A) comprises at least one organic $C_1$-$C_6$ alkoxysilane (A2) of formula (S-IV) selected from the group of Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane, and/or their condensation products.

The corresponding hydrolysis or condensation products are, for example, the following compounds:

Hydrolysis of $C_1$-$C_6$ alkoxy silane of the formula (S-I) with water (reaction scheme using the example of 3-aminopropyltriethoxysilane):

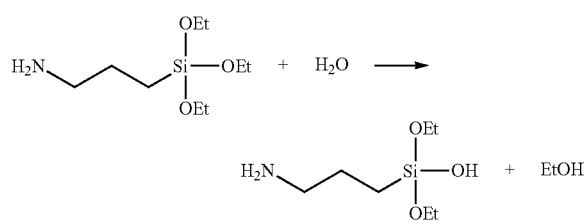

Depending on the amount of water used, the hydrolysis reaction can also take place several times per $C_1$-$C_6$ alkoxy silane used:

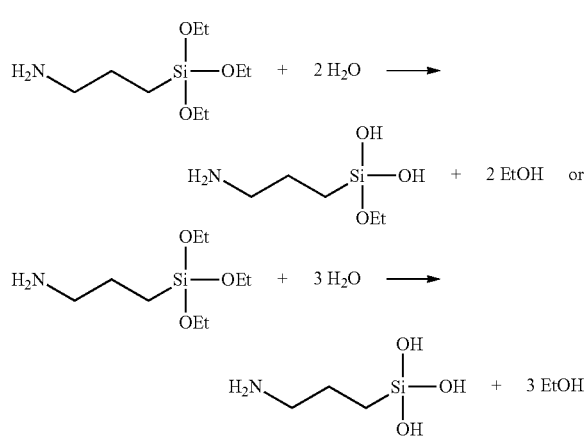

Hydrolysis of $C_1$-$C_6$ alkoxy silane of formula (S-IV) with water (reaction scheme using methyltrimethoxysilane as an example):

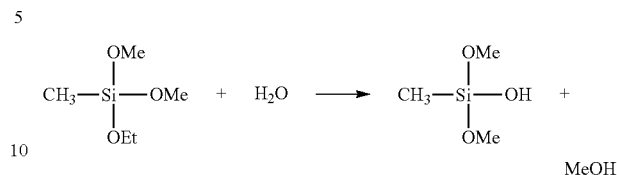

Depending on the amount of water used, the hydrolysis reaction can also take place several times per $C_1$-$C_6$ alkoxy silane used:

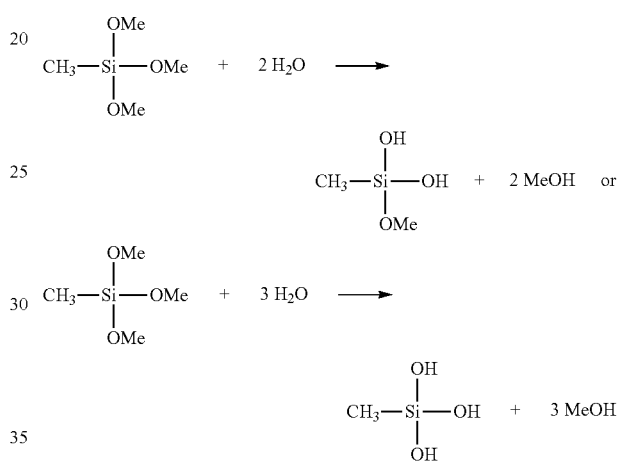

Possible condensation reactions include (shown using the mixture (3-aminopropyl)triethoxysilane and methyltrimethoxysilane):

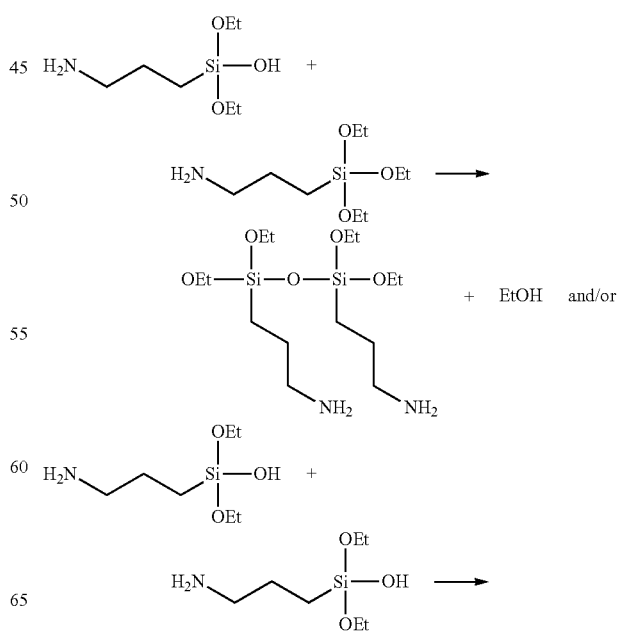

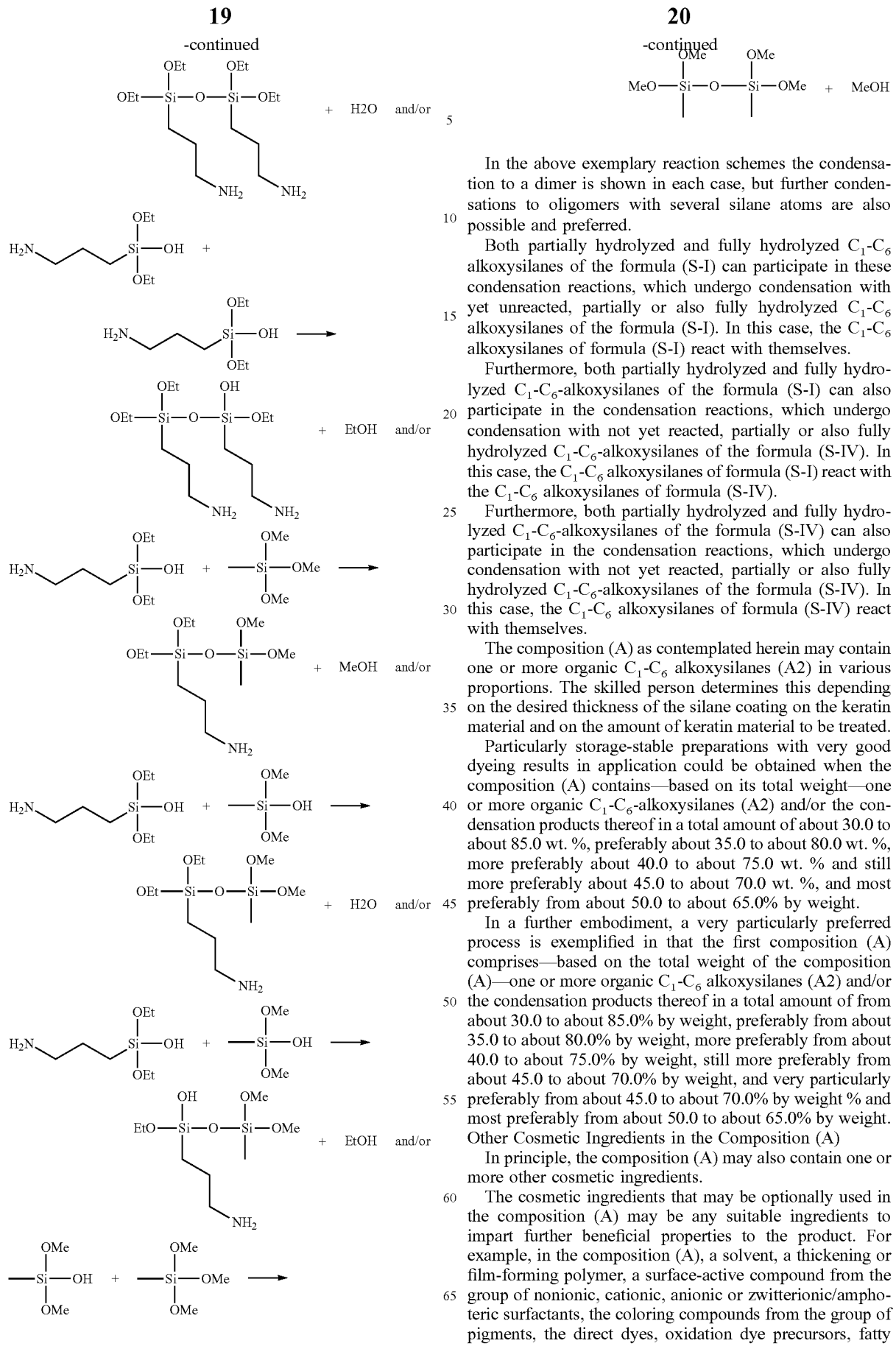

In the above exemplary reaction schemes the condensation to a dimer is shown in each case, but further condensations to oligomers with several silane atoms are also possible and preferred.

Both partially hydrolyzed and fully hydrolyzed $C_1$-$C_6$ alkoxysilanes of the formula (S-I) can participate in these condensation reactions, which undergo condensation with yet unreacted, partially or also fully hydrolyzed $C_1$-$C_6$ alkoxysilanes of the formula (S-I). In this case, the $C_1$-$C_6$ alkoxysilanes of formula (S-I) react with themselves.

Furthermore, both partially hydrolyzed and fully hydrolyzed $C_1$-$C_6$-alkoxysilanes of the formula (S-I) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and fully hydrolyzed $C_1$-$C_6$-alkoxysilanes of the formula (S-IV) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-IV) react with themselves.

The composition (A) as contemplated herein may contain one or more organic $C_1$-$C_6$ alkoxysilanes (A2) in various proportions. The skilled person determines this depending on the desired thickness of the silane coating on the keratin material and on the amount of keratin material to be treated.

Particularly storage-stable preparations with very good dyeing results in application could be obtained when the composition (A) contains—based on its total weight—one or more organic $C_1$-$C_6$-alkoxysilanes (A2) and/or the condensation products thereof in a total amount of about 30.0 to about 85.0 wt. %, preferably about 35.0 to about 80.0 wt. %, more preferably about 40.0 to about 75.0 wt. % and still more preferably about 45.0 to about 70.0 wt. %, and most preferably from about 50.0 to about 65.0% by weight.

In a further embodiment, a very particularly preferred process is exemplified in that the first composition (A) comprises—based on the total weight of the composition (A)—one or more organic $C_1$-$C_6$ alkoxysilanes (A2) and/or the condensation products thereof in a total amount of from about 30.0 to about 85.0% by weight, preferably from about 35.0 to about 80.0% by weight, more preferably from about 40.0 to about 75.0% by weight, still more preferably from about 45.0 to about 70.0% by weight, and very particularly preferably from about 45.0 to about 70.0% by weight % and most preferably from about 50.0 to about 65.0% by weight.

Other Cosmetic Ingredients in the Composition (A)

In principle, the composition (A) may also contain one or more other cosmetic ingredients.

The cosmetic ingredients that may be optionally used in the composition (A) may be any suitable ingredients to impart further beneficial properties to the product. For example, in the composition (A), a solvent, a thickening or film-forming polymer, a surface-active compound from the group of nonionic, cationic, anionic or zwitterionic/amphoteric surfactants, the coloring compounds from the group of pigments, the direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the specialist according to the desired properties of the agents. Regarding other optional components and the quantities of these components used, explicit reference is made to the relevant manuals known to the specialist.

However, as previously described, the organic $C_1$-$C_6$ alkoxysilanes (A2) can react not only with water but also with other cosmetic ingredients. To avoid these undesirable reactions, the preparations (A) with alkoxy silanes therefore preferably contain no other ingredients or only the selected ingredients that have been found to be chemically inert toward the $C_1$-$C_6$ alkoxy silanes. In this context, it has proved particularly preferred to use in composition (A) a cosmetic ingredient selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane.

In another particularly preferred embodiment, a process as contemplated herein is exemplified in that the first composition (A) comprises at least one cosmetic ingredient selected from the group of hexamethyldisiloxane, octamethyltrisiloxane, decamethyltetrasiloxane, hexamethylcyclotrisiloxane, octamethylcyclotetrasiloxane and decamethylcyclopentasiloxane. Hexamethyldisiloxane has the CAS number 107-46-0 and can be purchased commercially from Sigma-Aldrich®, for example.

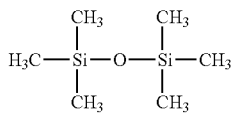

Octamethyltrisiloxane has the CAS number 107-51-7 and is also commercially available from Sigma-Aldrich®.

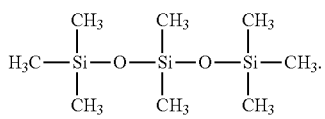

Decamethyltetrasiloxane carries the CAS number 141-62-8 and is also commercially available from Sigma-Aldrich®.

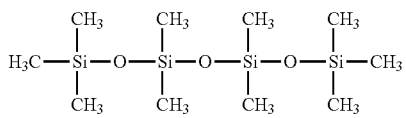

Hexamethylcyclotrisiloxane has the CAS No. 541-05-9.
Octamethylcyclotetrasiloxane has the CAS No. 556-67-2.
Decamethylcyclopentasiloxane has the CAS No. 541-02-6.

The use of hexamethyldisiloxane in composition (A) has proved to be particularly preferred. Particularly preferably, hexamethyldisiloxane is present—based on the total weight of composition (A)—in amounts of about 10.0 to about 50.0% by weight, preferably about 15.0 to about 45.0% by weight, further preferably about 20.0 to about 40.0% by weight, still further preferably about 25.0 to about 35.0% by weight and most preferably about 31.0 to about 34.0% by weight in composition (A).

In another very particularly preferred embodiment, a device as contemplated herein is exemplified in that the first composition (A) contains—based on the total weight of the composition (A)—about 10.0 to about 50.0% by weight, preferably about 15.0 to about 45.0% by weight, further preferably about 20.0 to about 40.0% by weight, still further preferably about 25.0 to about 35.0% by weight and very particularly preferably about 31.0 to about 34.0% by weight of hexamethyldisiloxane.

Preparation of the Composition (A),

In step (1) of the process as contemplated herein, the composition (A) is prepared. The preparation can be carried out, for example, by reacting or also reacting one or more organic $C_1$-$C_6$ alkoxy silanes with water. To initiate this reaction, the $C_1$-$C_6$ alkoxy silane(s) are preferably mixed with water.

The preparation can be carried out, for example, in a reaction vessel or reactor suitable for this purpose. Depending on the desired approach size, various prior art models are known and commercially available for this purpose.

For example, the reaction of the organic $C_1$-$C_6$ alkoxy silanes with water can be carried out in a reaction vessel or a reactor, preferably a double-walled reactor, a reactor with an external heat exchanger, a tubular reactor, a reactor with a thin-film evaporator, a reactor with a falling-film evaporator, and/or a reactor with an attached condenser.

In another particularly preferred embodiment, a process as contemplated herein is exemplified by:
(1) Preparation of the first composition (A) by mixing one or more organic $C_1$-$C_6$ alkoxy silanes with water in a reaction vessel or a reactor, preferably in a double-walled reactor, a reactor with external heat exchanger, a tubular reactor, a reactor with thin-film evaporator, a reactor with falling-film evaporator and/or a reactor with attached condenser.

A reaction vessel that is very suitable for smaller preparations is, for example, a glass flask commonly used for chemical reactions with a capacity of about 1 liter, about 3 liters or about 5 liters, such as a 3-liter single-neck or multi-neck flask with ground joints.

A reactor is a confined space (container, vessel) that has been specially designed and manufactured to allow certain reactions to take place and be controlled under defined conditions.

For larger approaches, it has proven advantageous to carry out the reaction in reactors made of metal. Typical reactors may include, for example, about a 10-liter, about 20-liter, or about 50-liter capacity. Larger reactors for the production area can also include fill volumes of about 100-liters, about 500-liters or about 1000-liters.

Double-wall reactors have two reactor shells or reactor walls, with a tempering fluid circulating in the area between the two walls. This enables particularly good adjustment of the temperature to the required values.

The use of reactors, in particular double-walled reactors with an enlarged heat exchange surface, has also proven to be particularly suitable, whereby the heat exchange can take place either through internal installations or using an external heat exchanger.

Corresponding reactors are, for example, laboratory reactors from the company IKA®. In this context, the models "LR-2.ST" or the model "magic plant" can be mentioned.

The reaction of the organic $C_1$-$C_6$ alkoxy silanes with water, which takes place in step (1), can occur in different ways. The reaction starts as soon as the $C_1$-$C_6$ alkoxy silanes meet water by mixing. One possibility is to place the desired amount of water in the reaction vessel or reactor and then add that or the $C_1$-$C_6$ alkoxy silanes.

In a further embodiment, it is also possible to first introduce the organic $C_1$-$C_6$ alkoxy silane(s) into the reaction vessel or reactor and then add the desired amount of water.

To produce particularly high-performance keratin treatment agents, the maintenance of specific temperature ranges has proven to be quite advantageous during the production in step (1).

In this context, it was found that a minimum temperature of about 20° C. in step (1) is particularly well suited to allow the hydrolysis to proceed at a sufficiently high rate and to ensure efficient reaction control.

On the other hand, however, heating of the reaction mixture to temperatures above about 70° C. should be avoided. If the production is carried out at too high temperatures, an undesirable or excessive polymerization or condensation reaction will probably take place at this point, resulting in the inability to form a film adhering to the keratin material during subsequent application of the agent. When using an agent produced at too high temperatures in a dyeing process, it was therefore no longer possible to achieve sufficiently high color intensities.

For these reasons, the reaction of the $C_1$-$C_6$ organic alkoxy silane(s) with water in step (1) of the process should be carried out at a temperature of about 20 to about 70° C.

Any other optional ingredients included in composition (A) may be added to composition (A), for example, following this reaction.

Following preparation, the composition (A) is preferably filled into a packaging unit.

The packaging unit can either be a final packaging from which the user takes the agent for treatment of the keratin materials. Suitable end-packages include a bottle, a tube, a jar, a can, a sachet, an aerosol pressure container, a non-aerosol pressure container. In this regard, these final packages may contain the keratin treatment agents in quantities sufficient for one, or if necessary, several applications. Preference is given to filling in a quantity sufficient for a single application.

Further, however, the composition (A) may also be filled into an intermediate package, which may be, for example, a canister or a hobbock. Filling into an intermediate package is particularly suitable if the reaction vessel or reactor in which the process as contemplated herein was carried out and the filling plant in which filling into the final package takes place are physically separated.

In another very particularly preferred embodiment, a method as contemplated herein is exemplified by the
(1) Preparation of a first composition (A) comprising
  (A1) less than about 10% by weight of water and
  (A2) one or more organic $C_1$-$C_6$ alkoxy silanes and/or condensation products thereof, and filling the composition (A) into a bottle, a tube, a jar, a can, a sachet, an aerosol pressure container, a non-aerosol pressure container, a canister or a hobbock.

The packaging units may be common, standard, commercially available containers used in cosmetics.

Composition (B)

Step (2) of the process as contemplated herein is exemplified by the preparation of the second composition (B). The composition (B) is exemplified in that it comprises
(B1) Water and
(B2) one or more fat components and
(B3) one or more colorant compounds selected from the group of pigments and/or direct dyes.

Water Content (B1) in the Composition (B)

Just before application on the keratinous material, the compositions (A) and (B) are mixed. Mixing (A) and (B) produces the keratin treatment agent ready for use, i.e., the silane blend (A), which is stable or capable of being stored, is converted into its reactive form by contact with the water-containing composition (B). Mixing of compositions (A) and (B) starts a polymerization reaction originating from the alkoxy-silane monomers or alkoxy-silane oligomers, which finally leads to the formation of the film or coating on the keratin material.

The more water meets the organic $C_1$-$C_6$ alkoxy silane(s), the greater the extent of the polymerization reaction. For example, if the composition (B) contains a lot of water (B1), the monomeric or oligomeric silane condensates previously present in the low-water composition (A) now polymerize very rapidly to form polymers of higher or high molecular weight. The high molecular weight silane polymers then form the film on the keratinous material. For this reason, water (B1) is an essential ingredient of the present disclosure of composition (B).

Particularly uniform colorations on the entire head could be obtained if composition (B) contains—based on the total weight of composition (B)—about 10.0 to about 90.0% by weight, preferably about 30.0 to about 90.0% by weight, more preferably about 50.0 to about 90.0% by weight, still more preferably about 70.0 to about 90.0% by weight and very particularly preferably about 75.0 to about 90.0% by weight of water (B1).

In another particularly preferred embodiment, a process as contemplated herein is exemplified in that the second composition (B) contains—based on the total weight of the composition (B)—about 10.0 to about 90.0% by weight, preferably about 30.0 to about 90.0% by weight, more preferably about 50.0 to about 90.0% by weight, still more preferably about 70.0 to about 90.0% by weight and very particularly preferably about 75.0 to about 90.0% by weight of water (B1).

Fat Components in the Composition (B)

A further feature of composition (B) is its content of at least one Fat component. Surprisingly, the use of at least one fatty ingredient has been found to optimize the reaction rate of the organic $C_1$-$C_6$ alkoxy silanes to allow uniform coloring over the entire head.

The fatty components are hydrophobic substances that can form emulsions in the presence of water, forming micelle systems. Without being committed to this theory, it is assumed that the $C_1$-$C_6$ alkoxysilanes—either in the form of their monomers or possibly in the form of their condensed oligomers—are embedded in this hydrophobic environment or in the micelle systems so that the polarity of their environment changes. Due to the hydrophobic nature of the fatty components, the environment of the $C_1$-$C_6$ alkoxysilanes is also hydrophobized. It is assumed that the polymerization reaction of the $C_1$-$C_6$ alkoxy silanes leading to the film or coating takes place in an environment of reduced polarity at reduced speed.

For the purposes of the present disclosure, "fatty components" means organic compounds with a solubility in water at room temperature (22° C.) and atmospheric pressure (760 mmHg) of less than about 1% by weight, preferably less than about 0.1% by weight. The definition of fat constituents explicitly covers only uncharged (i.e., non-ionic) compounds. Fat components have at least one saturated or unsaturated alkyl group with at least 12 C atoms. The molecular weight of the fat constituents is a maximum of about 5000 g/mol, preferably a maximum of about 2500 g/mol and particularly preferably a maximum of about 1000 g/mol. The fat components are neither polyoxyalkylated nor polyglycerolated compounds.

Very preferably, the fat components (B2) included in the composition (B) are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

In one embodiment, particularly good results were obtained when the second composition (B) contains one or more fat constituents (B2) from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

The $C_{12}$-$C_{30}$ fatty alcohols can be saturated, mono- or polyunsaturated, linear or branched fatty alcohols with about 12 to about 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

By selecting particularly well-suited fatty components, the polarity of the composition (B) can be optimally adjusted and the polymerization rate of the $C_1$-$C_6$ alkoxysilanes can be particularly well adapted to the respectively selected application conditions.

In this context, it has been found that the use of at least one $C_{12}$-$C_{30}$ fatty alcohol (B2) in the composition (B) creates an emulsion system in which the alkoxysilanes (A2) can be embedded particularly well.

In one embodiment, particularly good results were obtained when the second composition (B) comprises one or more $C_{12}$-$C_{30}$ fatty alcohols selected from the group of dodecan-1-ol (dodecyl alcohol, lauryl alcohol), Tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), Behenyl alcohol (docosan-1-ol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), Gadoleyl alcohol ((9Z)-Eicos-9-en-1-ol), Arachidone alcohol ((5Z,8Z,11Z,14Z)-Eicosa-5,8,11,14-tetraen-1-ol), Erucyl alcohol ((13Z)-Docos-13-en-1-ol), Brassidyl alcohol ((13E)-docosen-1-ol) 2-octyl-dodecanol, 2-hexyl-dodecanol and/or 2-butyl-dodecanol.

In a very particularly preferred embodiment, a process as contemplated herein is exemplified in that the second composition (B) comprises one or more $C_{12}$-$C_{30}$ fatty alcohols (B2) selected from the group of Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol.

By selecting the appropriate amounts of $C_{12}$-$C_{30}$ fatty alcohols (B2) to be used, the The speed of the film formation originating from the $C_1$-$C_6$ alkoxy silanes is particularly strongly co-determined. For this reason, it has proved particularly preferable to use one or more $C_{12}$-$C_{30}$ fatty alcohols (B2) in very specific quantity ranges.

It is particularly preferred if the second composition (B) comprises—based on the total weight of the composition (B)—one or more $C_{12}$-$C_{30}$ fatty alcohols (B2) in a total amount of from about 2.0 to about 50.0% by weight, preferably from about 3.0 to about 40.0% by weight, more preferably from about 4.0 to about 30.0% by weight, even more preferably from about 5.0 to about 20.0% by weight, and most preferably from about 6.0 to about 15.0% by weight.

In a further particularly preferred embodiment, a process as contemplated herein is exemplified in that the second composition (B) comprises—based on the total weight of the composition (B)—one or more $C_{12}$-$C_{30}$ fatty alcohols (B2) in a total amount of about 2.0 to about 50.0 wt. %, preferably from about 3.0 to about 40.0% by weight, more preferably from about 4.0 to about 30.0% by weight, still more preferably from about 5.0 to about 20.0% by weight and most preferably from about 6.0 to about 15.0% by weight.

Furthermore, as a very particularly preferred fat ingredient (B2), the composition (B) may also comprise at least one $C_{12}$-$C_{30}$ fatty acid triglyceride which is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, *Moringa* oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when composition (B) contained at least one $C_{12}$-$C_{30}$ fatty acid monoglyceride selected from the monoesters of glycerol with one equivalent of fatty acid selected from the group of dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In a particularly preferred embodiment, a process as contemplated herein is exemplified in that the second composition (B) comprises at least one $C_{12}$-$C_{30}$ fatty acid monoglyceride (B2) selected from the monoesters of glycerol with one equivalent of fatty acid selected from the group of dodecanoic acid, tetradecanoic acid, hexadecanoic acid, tetracosanoic acid, octadecanoic acid, eicosanoic acid and/or docosanoic acid.

The choice of suitable amounts of $C_{12}$-$C_{30}$ fatty acid mono-, $C_{12}$-$C_{30}$ fatty acid di- and/or $C_{12}$-$C_{30}$ fatty acid triglycerides can also have a particularly strong influence on the rate of film formation originating from the $C_1$-$C_6$ alkoxy silanes. For this reason, it has proven to be particularly preferred to use one or more $C_{12}$-$C_{30}$ fatty acid mono-, $C_{12}$-$C_{30}$ fatty acid di- and/or $C_{12}$-$C_{30}$ fatty acid triglycerides (B2) in very specific ranges of amounts in the composition (B).

With regard to the solution of the task as contemplated herein, it has proved to be quite particularly preferable if the second composition (B)—based on the total weight of the composition (B)—contained one or more $C_{12}$-$C_{30}$ fatty acid mono-, $C_{12}$-$C_{30}$ fatty acid di- and/or $C_{12}$-$C_{30}$ fatty acid triglycerides (B2) in a total amount of about 0.1 to about 20.0 wt. % by weight, preferably from about 0.3 to about 15.0% by weight, more preferably from about 0.5 to about 10.0% by weight and most preferably from about 0.8 to about 5.0% by weight.

In a very particularly preferred embodiment, a process as contemplated herein is exemplified in that the second composition (B) contains—based on the total weight of the composition (B)—one or more $C_{12}$-$C_{30}$ fatty acid mono-, $C_{12}$-$C_{30}$ fatty acid di- and/or $C_{12}$-$C_{30}$ fatty acid triglycerides (B2) in a total amount of about 0.1 to about 20.0 wt. % by weight, preferably from about 0.3 to about 15.0% by weight, further preferably from about 0.5 to about 10.0% by weight and most preferably from about 0.8 to about 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as sole fat components (B2) in the compositions (B). However, it is particularly preferred to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into composition (B).

Furthermore, as a very particularly preferred fatty ingredient (B2), the composition (B) may also contain at least one hydrocarbon.

Hydrocarbons are compounds formed exclusively of the atoms carbon and hydrogen with 8 to about 80 C atoms. In this context, aliphatic hydrocarbons such as mineral oils, liquid paraffin oils (e.g., Paraffinum Liquidum or Paraffinum Perliquidum), isoparaffin oils, semisolid paraffin oils, paraffin waxes, hard paraffin (Paraffinum *Solidum*), Vaseline and polydecenes are particularly preferred.

Liquid paraffin oils (Paraffinum Liquidum and Paraffinium Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, formed mainly of hydrocarbon chains with a C-chain distribution of about 25 to about 35 C-atoms.

Very particular good results were obtained when the composition (B) included at least one hydrocarbon (B2) selected from the group of mineral oils comprising liquid kerosene oils, isoparaffin oils, semisolid kerosene oils, kerosene waxes, hard kerosene (paraffinum *solidum*), petrolatum and polydecenes.

In a very particularly preferred embodiment, a process as contemplated herein is exemplified in that the second composition (B) comprises at least one fatty constituent (B2) from the group of hydrocarbons.

The speed of film formation from the $C_1$-$C_6$ alkoxy silanes can also be particularly strongly influenced by the choice of suitable quantities of hydrocarbons. For this reason, it has been found to be particularly preferable to use one or more hydrocarbons in very specific ranges of amounts in composition (B).

Regarding the solution of the problem as contemplated herein, it proved to be quite particularly preferable if the second composition (B) contained—based on the total weight of the composition (B)—one or more hydrocarbons (B2) in a total amount of from about 0.5 to about 20.0% by weight, preferably from about 1.0 to about 15.0% by weight, more preferably from about 1.5 to about 10.0% by weight and most preferably from about 2.0 to about 8.0% by weight.

In a very particularly preferred embodiment, a process as contemplated herein is exemplified in that the second composition (B) contains—based on the total weight of the composition (B)—one or more hydrocarbons (B2) in a total amount of from about 0.5 to about 20.0% by weight, preferably from about 1.0 to about 15.0% by weight, more preferably from about 1.5 to about 10.0% by weight and very particularly preferably from about 2.0 to about 8.0% by weight.

The hydrocarbon(s) may be used as the sole fatty constituent(s) (B2) in the composition(s) (B). However, it is particularly preferred to incorporate at least one hydrocarbon in combination with at least one other component in the compositions (B).

Very preferably, the composition (B) contains at least one fatty constituent (B2) from the group of $C_{12}$-$C_{30}$ fatty alcohols and at least one further fatty constituent from the group of hydrocarbons.

Surfactants in the Composition (B)

Due to its content of water (B1) and fat component (B2), the composition (B) is in the form of an emulsion. To further optimize the formation of the emulsion, it has proven to be particularly preferred to further use at least one surfactant in the composition (B). Quite preferably, therefore, the composition (B) additionally optionally contains at least one surfactant.

In the context of a further particularly preferred embodiment, a process as contemplated herein is exemplified in that the second composition (B) comprises at least one surfactant.

The term surfactants (T) refer to surface-active substances that can form adsorption layers on surfaces and interfaces or aggregate in bulk phases to form micelle colloids or lyotropic mesophases. A distinction is made between anionic surfactants consisting of a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In the context of a very particularly preferred embodiment, a process as contemplated herein is exemplified in that the second composition (B) comprises at least one surfactant, particularly preferably at least one nonionic surfactant.

Non-ionic surfactants contain, for example, a polyol group, a polyalkylene glycol ether group or a combination of polyol and polyglycol ether group as the hydrophilic group. Such links include Addition products of about 2 to about 50 mol ethylene oxide and/or 0 to 5 mol propylene oxide to linear and branched fatty alcohols with 6 to about 30 C atoms, the fatty alcohol polyglycol ethers or the fatty alcohol polypropylene glycol ethers or mixed fatty alcohol polyethers, Addition products of about 2 to about 50 mol ethylene oxide and/or 0 to about 5 mol propylene oxide to linear and branched fatty acids with 6 to about 30 C atoms, the fatty acid polyglycol ethers or the fatty acid polypropylene glycol ethers or mixed fatty acid polyethers, Addition products of about 2 to about 50 mol ethylene oxide and/or 0 to about 5 mol propylene oxide to linear and branched alkylphenols having 8 to about 15 C atoms in the alkyl group, the alkylphenol polyglycol ethers or the alkylpolypropylene glycol ethers or mixed alkylphenol polyethers, with a methyl or $C_2$-$C_6$- alkyl radical end-group capped addition products of about 2 to about 50 moles of ethylene oxide and/or 0 to about 5 moles of propylene oxide to linear and branched fatty alcohols with 8 to about 30 C atoms, to fatty acids with 8 to about 30 C atoms and to alkylphenols with 8 to about 15 C atoms in the alkyl group, such as the grades available under the sales names Dehydol® LS, Dehydol® LT (Cognis), $C_{12}$-$C_{30}$ fatty acid mono- and diesters of addition products of about 1 to about 30 mol ethylene oxide to glycerol, Addition products of about 5 to about 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

$$R^1CO-(OCH_2CHR^2)_wOR^3 \qquad \text{(Tnio-1)}$$

in which $R^1CO$ is a linear or branched, saturated and/or unsaturated acyl radical having 6 to about 22 carbon atoms, $R^2$ is hydrogen or methyl, $R^3$ is linear or branched alkyl radicals having 1 to 4 carbon atoms and w is numbers from 1 to about 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (E4-II), $$R^4O\text{-}[G]_p \tag{Tnio-2}$$

in which $R^4$ is an alkyl or alkenyl radical containing 4 to about 22 carbon atoms, G is a sugar residue containing 5 or 6 carbon atoms and p is several 1 to about 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e., the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of about 1.1 to about 3.0 are used. From an application technology point of view, those alkyl and/or alkenyl oligoglycosides are preferred whose degree of oligomerization is less than about 1.7 and lies between about 1.2 and about 1.4. The alkyl or alkenyl radical $R^4$ can be derived from primary alcohols containing 4 to about 11, preferably 8 to about 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6% by weight of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having about 12 to about 22, preferably about 12 to about 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Sugar surfactants of the fatty acid N-alkyl polyhydroxyalkylamide type, a nonionic surfactant of formula (Tnio-3)

$$R^5CO\text{—}NR^6\text{—}[Z] \tag{Tnio-3}$$

in which $R^5CO$ is an aliphatic acyl radical containing 6 to 22 carbon atoms, $R^6$ is hydrogen, an alkyl or hydroxyalkyl radical containing 1 to 4 carbon atoms and [Z] is a linear or branched polyhydroxyalkyl radical containing 3 to about 12 carbon atoms and 3 to about 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO\text{—}(NR^8)\text{—}CH_2\text{—}[CH(OH)]_4\text{—}CH_2OH \tag{Tnio-4}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palm oleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the compositions used as contemplated herein in amounts of about 0.1-about 20% by weight, based on the total composition. Amounts of about 0.5-about 15 wt. % are preferred and amounts of about 0.5-about 7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with about 2 to about 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to about 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Very particularly good results were obtained when a second composition (B) containing at least one ethoxylated fatty alcohol with a degree of ethoxylation of about 10 to about 40 was used in the process as contemplated herein.

In another very particularly preferred embodiment, a process as contemplated herein is exemplified in that the second composition (B) comprises at least one nonionic surfactant of the formula (T-I),

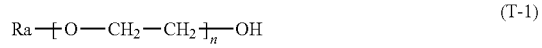

(T-1)

wherein

Ra represents a saturated or unsaturated, unbranched or branched $C_8$-$C_{24}$ alkyl group, preferably a saturated, unbranched $C_{16}$- to $C_{18}$ alkyl group, and n is an integer from about 10 to about 40, preferably an integer from about 20 to about 35, and particularly preferably the number 30.

A particularly well-suited nonionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin® B3 from BASF®.

The nonionic surfactants of the formula (T-I) may preferably be present in the preparation (B) used as contemplated herein in amounts of about 0.1-about 20% by weight, based on the total weight of the preparation (B). Amounts of about 0.5-about 15 wt. % are preferred and amounts of about 0.5-about 7.5 wt. % are particularly preferred.

Coloring Compounds

As a third constituent (B3) essential to the present disclosure, the composition (B) as contemplated herein contains at least one colorant compound selected from the group of pigments and/or direct dyes.

The colorant compound(s) may preferably be selected from the pigments and/or the direct dyes. The group of direct dyes also includes photochromic dyes and thermochromic dyes.

Pigments within the meaning of the present disclosure are coloring compounds which have a solubility in water at 25° C. of less than about 0.5 g/L, preferably less than about 0.1 g/L, even more preferably less than about 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, a composition as contemplated herein is exemplified in that it comprises at least one colorant compound selected from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. The use of pigments made of metals or metal alloys are also particularly suitable. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

Colored pearlescent pigments are also particularly preferred colorants from the group of pigments as contemplated herein. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

In a very particularly preferred embodiment, a process as contemplated herein is exemplified in that the second composition (B) comprises at least one coloring compound selected from the group of inorganic pigments, where the inorganic pigments are selected from the group of colored metal oxides, metal hydroxides, metal oxide hydrates, silicates, metal sulfides, complex metal cyanides, metal sulfates, bronze pigments, metals, metal alloys and/or colored mica- or mica-based pigments coated with at least one metal oxide and/or a metal oxychloride.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, the composition (B) as contemplated herein is exemplified in that it comprises at least one colorant compound from the group of pigments selected from the group of colored metal oxides, metal hydroxides, metal oxide hydrates, silicates, metal sulfides, complex metal cyanides, metal sulfates, bronze pigments and/or from mica- or mica-based colorant compounds coated with at least one metal oxide and/or a metal oxychloride.

In a further preferred embodiment, a composition (B) as contemplated herein is exemplified in that it comprises at least one colorant compound selected from mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors and Sunshine® from Sunstar.

Particularly preferred color pigments with the trade name Colorona® are, for example:
Colorona® Copper, Merck®, MICA, CI 77491 (IRON OXIDES)
Colorona® Passion Orange, Merck®, Mica, CI 77491 (Iron Oxides), Alumina
Colorona® Patina Silver, Merck®, MICA, CI 77499 (IRON OXIDES), CI 77891 (TITANIUM DIOXIDE)
Colorona® RY, Merck®, CI 77891 (TITANIUM DIOXIDE), MICA, CI 75470 (CARMINE)
Colorona® Oriental Beige, Merck®, MICA, CI 77891 (TITANIUM DIOXIDE), CI 77491 (IRON OXIDES)
Colorona® Dark Blue, Merck®, MICA, TITANIUM DIOXIDE, FERRIC FERROCYANIDE
Colorona® Chameleon, Merck®, CI 77491 (IRON OXIDES), MICA
Colorona® Aborigine Amber, Merck®, MICA, CI 77499 (IRON OXIDES), CI 77891 (TITANIUM DIOXIDE)
Colorona® Blackstar Blue, Merck®, CI 77499 (IRON OXIDES), MICA
Colorona® Patagonian Purple, Merck®, MICA, CI 77491 (IRON OXIDES), CI 77891 (TITANIUM DIOXIDE), CI 77510 (FERRIC FERROCYANIDE)
Colorona® Red Brown, Merck®, MICA, CI 77491 (IRON OXIDES), CI 77891 (TITANIUM DIOXIDE)
Colorona® Russet, Merck®, CI 77491 (TITANIUM DIOXIDE), MICA, CI 77891 (IRON OXIDES)
Colorona® Imperial Red, Merck®, MICA, TITANIUM DIOXIDE (CI 77891), D&C RED NO. 30 (CI 73360)
Colorona® Majestic Green, Merck®, CI 77891 (TITANIUM DIOXIDE), MICA, CI 77288 (CHROMIUM OXIDE GREENS)
Colorona® Light Blue, Merck®, MICA, TITANIUM DIOXIDE (CI 77891), FERRIC FERROCYANIDE (CI 77510)
Colorona® Red Gold, Merck®, MICA, CI 77891 (TITANIUM DIOXIDE), CI 77491 (IRON OXIDES)
Colorona® Gold Plus MP 25, Merck®, MICA, TITANIUM DIOXIDE (CI 77891), IRON OXIDES (CI 77491)
Colorona® Carmine Red, Merck®, MICA, TITANIUM DIOXIDE, CARMINE
Colorona® Blackstar Green, Merck®, MICA, CI 77499 (IRON OXIDES)
Colorona® Bordeaux, Merck®, MICA, CI 77491 (IRON OXIDES)
Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name Unipure® are for example:
Unipure® Red LC 381 EM, Sensient® CI 77491 (Iron Oxides), Silica
Unipure® Black LC 989 EM, Sensient®, CI 77499 (Iron Oxides), Silica
Unipure® Yellow LC 182 EM, Sensient®, CI 77492 (Iron Oxides), Silica In a further preferred embodiment, the composition (B) as contemplated herein is exemplified in that it comprises at least one color-imparting compound from the group of pigments selected from the group of metals and metal alloys, in particular aluminum and aluminum alloys.

Particularly preferred color pigments of this type can be purchased commercially under the trade name Alegrace® from the Schlenk® company:
Alegrace® Gorgeous B 56/77-1 Vibrant Silver
Alegrace® Spectacular A 35/00-1, Elegant Iris
Alegrace® Spectacular A 20/00-1, Tender Iris
Alegrace® Spectacular A 150/00-1, Fancy Iris
Alegrace® Marvelous A 12/77-1 Bright Silver
Alegrace® Marvelous A 12/77-2 Platinum Silver
Alegrace® Marvelous A 12/77-3 White Silver
Alegrace® Marvelous D 12/77-1 Shiny Silver
Alegrace® Lustrous A 100/77-1 Smooth Silver
Alegrace® Lustrous A 150/771-1 Vivid Silver
Alegrace® Lustrous A 450/77-1 Intense Silver
Alegrace® Aurous A 21/11-1 Yellow Gold
Alegrace® Aurous A 21/71-1 White Gold In a further embodiment, the composition or preparation as contemplated herein may also contain one or more colorant compounds selected from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindigo, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a process as contemplated herein is exemplified in that the composition (B) comprises at least one colorant compound from the group of organic pigments selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The use of very specific pigments in preparation (B) has proven to be particularly suitable for producing especially uniform and natural color shades. Particularly intense and uniform colorations could be obtained if the composition (B) used in the process of the present disclosure contained at least one colorant compound (B3) selected from the group of the blue pigment having the color index number CI 74160, the yellow pigment having the color index number CI 11680, and the red pigment having the color index number CI 12490.

In another particularly preferred embodiment, a process as contemplated herein is exemplified in that the composition (B) comprises at least one coloring compound (B3) selected from the group of organic pigments selected from the group of
the blue pigment with the color index number CI 74160,
the yellow pigment with the color index number CI 11680, and
the red pigment with the color index number CI 12490.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilicate, calcium aluminum borosilicate or even aluminum.

For example, alizarin color varnish can be used.

Due to their excellent resistance to light and temperature, the use of the pigments as contemplated herein is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D_{50}$ of about 1.0 to about 50 μm, preferably about 5.0 to about 45 μm, preferably about 10 to about 40 μm, preferably about 14 to about 30 μm. The mean particle size $D_{50}$, for example, can be determined using dynamic light scattering (DLS).

The pigment or pigments may be used in an amount of from about 0.001 to about 20% by weight, from about 0.05 to about 5% by weight, in each case based on the total weight of the composition or preparation as contemplated herein.

As colorant compounds, the compositions as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than about 0.5 g/L and are therefore not to be regarded as pigments. Preferably, the direct dyes within the meaning of the present disclosure have a solubility in water (760 mmHg) at 25° C. of more than about 1.0 g/L. In particular, the direct dyes within the meaning of the present disclosure have a solubility in water (760 mmHg) at 25° C. of more than about 1.5 g/L.

Direct dyes can be divided into anionic, cationic and nonionic direct dyes.

In a further preferred embodiment, an agent as contemplated herein is exemplified in that it contains at least one anionic, cationic and/or nonionic direct dye as the coloring compound.

In a further preferred embodiment, a process as contemplated herein is exemplified in that the composition (B) and/or the composition (C) comprises at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—$SO_3H$). Depending on the pH value, the protonated forms (—COOH, —$SO_3H$) of the carboxylic acid or sulphonic acid groups are in equilibrium with their deprotonated forms (—$OO^-$, —$SO_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (760 mmHg) at 25° C. of more than about 0.5 g/L and are therefore not to be regarded as pigments. Preferably the acid dyes within the meaning of the present disclosure have a solubility in water (760 mmHg) at 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (25° C., 760 mmHg), they do not fall under the definition of a direct dye.

An essential feature of acid dyes is their ability to form anionic charges, whereby the carboxylic acid or sulphonic acid groups responsible for this are usually linked to different chromophoric systems. Suitable chromphoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF®), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange 11, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red No. 2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodofluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatrium salt of 7-hydroxy-8-[(E)-(4-sulfonato-1-naphthyl)-diazenyl)]-1,3-naphthalene disulfonate and has a very high water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonato-benzyl)imino]-2,5-cyclohexadien-1-ylidene}methyl)-benzenesulfonate and has a solubility in water of more than 20% by weight (25° C.).

Thermochromic dyes can also be used. Thermochromism involves the property of a material to change its color reversibly or irreversibly as a function of temperature. This can be done by changing both the intensity and/or the wavelength maximum.

Finally, it is also possible to use photochromic dyes. Photochromism involves the property of a material to change its color depending reversibly or irreversibly on irradiation with light, especially UV light. This can be done by changing both the intensity and/or the wavelength maximum.

The skilled person can select the amounts of coloring compounds (B3) used in the composition (B) depending on the desired color intensity and color shade. Particularly good results were obtained when the second composition (B)

contained—based on the total weight of the composition (B)—one or more coloring compounds (B3) in a total amount of about 0.1 to about 6.0 wt. %, preferably from about 0.3 to about 5.0% by weight, more preferably from about 0.5 to about 4.0% by weight and most preferably from about 0.7 to about 1.5% by weight.

In another particularly preferred embodiment, a process as contemplated herein is exemplified in that the composition (B) contains—based on the total weight of the composition (B)—one or more coloring compounds (B3) in a total amount of from about 0.1 to about 6.0% by weight, preferably from about 0.3 to about 5.0% by weight, more preferably from about 0.5 to about 4.0% by weight and very particularly preferably from about 0.7 to about 1.5% by weight.

In another particularly preferred embodiment, a process as contemplated herein is exemplified in that the composition (B) contains—based on the total weight of the composition (B)—one or more pigments (B3) in a total amount of from about 0.1 to about 6.0% by weight, preferably from about 0.3 to about 5.0% by weight, more preferably from about 0.5 to about 4.0% by weight and very particularly preferably from about 0.7 to about 1.5% by weight.

Other Cosmetic Ingredients in the Composition (B)

In addition to the essential and optional ingredients of the present disclosure already described above, the composition (B) may further comprise one or more additional cosmetic ingredients.

The cosmetic ingredients that may be optionally used in the composition (B) may be any suitable ingredients to impart further beneficial properties to the product. For example, in the composition (A), a solvent, a thickening or film-forming polymer, a surface-active compound from the group of nonionic, cationic, anionic or zwitterionic/amphoteric surfactants, the coloring compounds from the group of pigments, the direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the specialist according to the desired properties of the agents. Regarding other optional components and the quantities of these components used, explicit reference is made to the relevant manuals known to the specialist.

Preparation of the Composition (B)

The composition (B) prepared in step (2) of the process as contemplated herein is an emulsion which, in addition to water and the fatty constituent(s), also contains the coloring compound(s). The production can be carried out, for example, according to the usual processes known to the skilled person.

One way of preparing the emulsion (B) is to first melt the fat components (B2), then add water (B1) while homogenizing, for example by stirring, and subsequently add the coloring compounds (B3).

The preparation can be carried out, for example, in a reaction vessel or reactor suitable for this purpose. Depending on the desired approach size, various prior art models are known and commercially available for this purpose. Particularly preferably, the composition (B) is prepared in a vessel with stirrer or homogenizer.

pH Values of the Compositions in the Process

In further experiments, it has been found that the pH values of compositions (A) and/or (B) can have an influence on the hydrolysis or condensation reactions that take place during application as described above. It was found that alkaline pH values in particular stop condensation at the oligomer stage. The more acidic the reaction mixture, the stronger the condensation seems to proceed and the higher the molecular weight of the silane condensates formed during condensation. For this reason, it is preferred that compositions (A) and/or (B) have a pH value from about 7.0 to about 12.0, preferably from about 7.5 to about 11.5, more preferably from about 8.5 to about 11.0, and most preferably from about 9.0 to about 11.0.

The water content of composition (A) is at most about 10.0% by weight and is preferably set even lower. In some embodiments, the water content of composition (B) may also be selected to be low. Particularly in the case of compositions with a very low water content, measuring the pH with the usual methods known from the prior art (pH value measurement by employing glass electrodes via combination electrodes or via pH indicator paper) can prove difficult. For this reason, the pH values as contemplated herein are those obtained after mixing or diluting the preparation in a about 1:1 ratio by weight with distilled water.

Accordingly, the corresponding pH is measured after, for example, about 50 g of the composition as contemplated herein has been mixed with about 50 g of distilled water.

In another very particularly preferred embodiment, a process as contemplated herein, is exemplified in that the composition (A) and/or (B), after dilution with distilled water in a weight ratio of about 1:1, has a pH of from about 7.0 to about 11.5, further preferably from about 8.5 to about 11.0 and very particularly preferably from about 9.0 to about 11.0.

To adjust this alkaline pH, it may be necessary to add an alkalizing agent and/or acidifying agent to the reaction mixture. The pH values for the purposes of the present disclosure are pH values measured at a temperature of 22° C.

For example, ammonia, alkanolamines and/or basic amino acids can be used as alkalizing agents.

Alkanolamines may be selected from primary amines having a $C_2$-$C_6$ alkyl parent bearing at least one hydroxyl group. Preferred alkanolamines are selected from the group formed by 2-aminoethane-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

For the purposes of the present disclosure, an amino acid is an organic compound comprising in its structure at least one protonatable amino group and at least one —COOH or one —SO$_3$H group. Preferred amino acids are aminocarboxylic acids, especially α-(alpha)-aminocarboxylic acids and w-aminocarboxylic acids, whereby α-aminocarboxylic acids are particularly preferred.

As contemplated herein, basic amino acids are those amino acids which have an isoelectric point pI of greater than about 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, inorganic alkalizing agents can also be used. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Apart from the alkalizing agents described above, experts are familiar with common acidifying agents for fine adjustment of the pH value. As contemplated herein, preferred acidifiers are pleasure acids, such as citric acid, acetic acid, malic acid or tartaric acid, as well as diluted mineral acids.

Following preparation, the composition (B) is preferably filled into a packaging unit.

The packaging unit can either be a final packaging from which the user takes the agent for treatment of the keratin materials. Suitable end-packages include a bottle, a tube, a jar, a can, a sachet, an aerosol pressure container, a non-aerosol pressure container. In this regard, these final packages may contain the keratin treatment agents in quantities sufficient for one, or if necessary, several applications. Preference is given to filling in a quantity sufficient for a single application.

Further, however, the composition (B) may also be filled into an intermediate package, which may be, for example, a canister or a hobbock. Filling into an intermediate package is particularly suitable if the reaction vessel or reactor in which the process as contemplated herein was carried out and the filling plant in which filling into the final package takes place are physically separated.

In another very particularly preferred embodiment, a method as contemplated herein is exemplified by the
(2) Preparation of a second composition (B) containing
   (B1) Water and
   (B2) one or more fat components and
   (B3) one or more colorant compounds selected from the group of pigments and/or direct dyes,
   and filling the composition (A) into a bottle, a tube, a jar, a can, a sachet, an aerosol pressure container, a non-aerosol pressure container, a canister or a hobbock.

The packaging units may be common, standard, commercially available containers used in cosmetics.

Storage of Composition (A) and/or (B)

The step (3) of the process as contemplated herein is exemplified by the storage of the composition (A) and/or (B) for a period of at least about 24 hours.

This step has proved to be essential to the achievement of particularly good color fastness properties.

In step (3), the compositions (A) and (B), which have preferably each been filled into a suitable packaging unit after their preparation, are stored in this packaging unit for a period of at least about 24 hours.

The packaging unit is in a sealed state during storage. This can be done, for example, by placing the sealed packaging units in a storage room or warehouse for at least about 24 hours at a time.

For the purposes of the present disclosure, storage of composition (A) or (B) in the packaging unit is understood to mean not opening the sealed packaging unit for a period of at least about 24 hours. Since the preparation is in a sealed packaging unit during storage, it does not meet the humidity outside the packaging unit or with oxygen.

The sealed packaging unit may be, for example, a bottle, a tube, ajar, a can, a sachet, an aerosol pressure container, a non-aerosol pressure container, a canister or a hobbock, each closed with a suitable lid.

The packaging units that can be used are those usually used in the field of cosmetics, made of the usual materials. These packaging units are known to the skilled person and are commercially available.

The capacity of the packaging unit will depend on the required application quantities. For example, a bottle closed with a tight lid, preferably a screw cap with a seal, with a volume of about 20 ml, about 50 ml, about 100 ml, about 250 ml, about 500 ml, or even about 1000 ml can be used as the bottle.

For example, a tube with a screw cap or also with a hinged hinge cap with a capacity of about 20 ml, about 50 ml, about 100 ml, about 250 ml, about 500 ml, or also about 1000 ml can be used as a tube. It is particularly preferred to seal the tube and to open the seal by using the lid only shortly before application.

Cans can also be provided with a screw cap with a seal and have, for example, a capacity of about 20 ml, about 50 ml, about 100 ml, about 250 ml, about 500 ml, or even about 1000 ml.

In this context, the sachet is also an inexpensive form of packaging with low material consumption. A sachet is a small package in the shape of a pocket or bag, often used in the packaging of cosmetics. For example, a typical sachet can be made by bonding or hot-pressing two films on top of each other, with bonding occurring at all edges of the films. The interior of the sachet (i.e., the pouch) produced by the bonding process can then be filled with the desired cosmetic preparation. The opening of the sachet can be done by tearing or cutting the sachet.

If storage is to take place in an intermediate container from which the preparation is transferred again in a further step into the final packaging used by the user, canisters or also hobbocks are suitable as packaging units. These usually have a larger capacity of about 1 liter, about 5 liters, about 10 liters, about 20 liters or even about 50 liters.

Without being committed to this theory, it is assumed in this context for preparation (A) that the hydrolysis reactions initiated by mixing the $C_1$-$C_6$ alkoxy silanes (A2) with water (A1) are not yet completed upon completion of the preparation of preparation (A) but continue to take place in the packaging unit over a period of several hours, preferably several days.

Presumably, the condensation reactions taking place in composition (A) lead to the formation of oligomeric molecular assemblies, which must have a certain minimum size to form a resistant film on the keratin material with sufficient rapidity. In the course of the work leading to the present disclosure, it was found that good and intense colorations could be obtained when the preparations were used in a dyeing process, especially when the preparation (A) was stored for a period of at least about 5 days.

In another very particularly preferred embodiment, a method as contemplated herein is exemplified by the
(3) Storing the composition (A) for a period of at least about 5 days, preferably at least about 10 days, more preferably at least about 14 days, and most preferably at least about 21 days.

In another very particularly preferred embodiment, a method as contemplated herein is exemplified by the
(3) Storing the composition (A) in a packaging unit for a period of at least about 5 days, preferably at least about 10 days, more preferably at least about 14 days, and most preferably at least about 21 days.

Storage of the composition (A) is particularly preferred within certain temperature ranges. In this context, it has proved particularly advantageous to maintain specific temperature ranges during the storage period, which takes place directly after production in step (1). Very good dyeing results were obtained when the preparation (A) was stored in the packaging unit at a temperature of from about 15° C. to about 40° C., preferably from about 15° C. to about 35° C. and particularly preferably from about 15° C. to about 25° C.

In another very particularly preferred embodiment, a method as contemplated herein is exemplified by the
(3) Storing the composition (A) for a period of at least about 5 days, preferably at least about 10 days, more preferably at least about 14 days, and most preferably at least about 21 days at a temperature in the range of from about 15° C. to about 40° C., preferably from about 15° C. to about 35° C., and most preferably from about 15° C. to about 25° C.

Under the given storage conditions, especially within the temperature ranges, the condensation reaction of the silanes seems to come to a standstill after some time, so that a longer storage does not show any negative influence on a later dyeing result. For example, the preparations (A) can be stored in a sealed packaging unit for a period of up to about 365 days at a temperature of about 15 to about 40° C. Since the packaging unit is sealed during storage, thus preventing contact with the outside air, which may be humid, longer storage periods than about 365 days are also possible.

In another very particularly preferred embodiment, a method as contemplated herein is exemplified by the
(3) Storing the preparation (A), preferably in a sealed packaging unit, for a period of from about 5 to about 365 days, preferably from about 10 to about 365 days, more preferably for a period of from about 14 to about 365 days, and especially preferably for a period of from about 21 to about 365 days.

In further tests, it has been shown that when using the process as contemplated herein, particularly washfast colorations could also be obtained when the composition (B) was stored for a period of at least about 24 hours.

Without being committed to this theory, a possible reason for the improvement in wash fastness could be that the colorant compounds (B3) contained in the composition (B), the pigments, become increasingly incorporated into the hydrophobic regions of the emulsion during storage, so that storage allows increased interaction of the fatty components (B2) and the colorant compounds (B3), resulting in more resistant coloration. It was found that this interaction requires a period of at least about 24 hours. Preferred is even longer storage for a period of at least about 48 hours (about 2 days), more preferred at least about 5 days and most preferred at least about 10 days.

In another very particularly preferred embodiment, a method as contemplated herein is exemplified by the
(3) Storing the composition (B) for a period of at least about 24 hours, preferably at least about 2 days, even more preferably at least about 5 days, and most preferably at least about 10 days.

In another very particularly preferred embodiment, a method as contemplated herein is exemplified by the
(3) Storing the composition (B) in a packaging unit for a period of at least about 24 hours, preferably at least about 2 days, even more preferably at least about 5 days, and most preferably at least about 10 days.

Storage of the composition (B) is also particularly preferred within certain temperature ranges. In this context, it has proved particularly advantageous to maintain specific temperature ranges during the storage period, which takes place directly after production in step (2). Very good dyeing results were obtained when the preparation (A) was stored in the packaging unit at a temperature of from about 15° C. to about 40° C., preferably from about 15° C. to about 35° C. and particularly preferably from about 15° C. to about 25° C.

In another very particularly preferred embodiment, a method as contemplated herein is exemplified by the
(3) Storing the composition (B) for a period of at least about 24 hours, preferably at least about 2 days, still more preferably at least about 5 days, and most preferably at least about 10 days, at a temperature in the range of from about 15° C. to about 40° C., preferably from about 15° C. to about 35° C., and most preferably from about 15° C. to about 25° C.

The compositions (B) have also been found to be stable emulsion systems, so that storage beyond the minimum period does not have a negative effect on the compositions (B), especially if the compositions (B) are stored in a sealed packaging unit. For this reason, longer storage periods than about 365 days are also possible for compositions (B).

In another very particularly preferred embodiment, a method as contemplated herein is exemplified by the
(3) Storing the composition (B) for a period of from about 24 hours to about 365 days, preferably from at least about 2 to about 365 days, even more preferably from at least about 5 to about 365 days, and most preferably from at least about 10 to about 365 days.

Mixture of Compositions (A) and (B)

In step (4) of the process as contemplated herein, the two compositions (A) and (B) are mixed. In this way, the ready-to-use agent for coloring the keratinous material is produced.

The work leading to the present disclosure has shown that composition (B) containing water (B1), fatty components (B2) and coloring compounds (B3) can have an optimum effect on the low-water silane blend (i.e., composition (A)), especially when compositions (A) and (B) have been mixed before use.

This mixing can be done, for example, by stirring or shaking. It is particularly advantageous to prepare the two compositions (A) and (B) separately in two containers and then, before use, to transfer the entire amount of composition (A) from its container to the container containing the second composition (B). It is particularly preferred to support the mixing process by shaking.

In a very particularly preferred embodiment, a process as contemplated herein is exemplified in that a composition is applied to the keratinous material, which composition was prepared immediately before application by shaking the first composition (A) and the second composition (B).

The two compositions (A) and (B) can be mixed in different proportions. For example, it is possible to mix about 10 parts by weight of composition (A) with about 1 part by weight of composition (B).

Particularly preferably, composition (A) is used in the form of a relatively highly concentrated, low-water silane blend, which is quasi-diluted by mixing with composition (B). For this reason, it is particularly preferred to mix composition (A) with an excess weight of composition (B). For example, about 1 part by weight of (A) can be mixed with about 20 parts by weight of (B), or about 1 part by weight of (A) can be mixed with about 1 part by weight of (B), or about 1 part by weight of (A) can be mixed with about 5 parts by weight of (B), or about 1 part by weight of (A) can be mixed with about 10 parts by weight of (B).

In the context of a further particularly preferred embodiment, a process as contemplated herein is exemplified by mixing the compositions (A) and (B) in a weight/volume ratio (A)/(B) of from about 1:20 to about 20:1, preferably from about 1:5 to about 1:20, and most preferably from about 1:6 to about 1:14.

Application of the Mixture of (A) and (B) on the Keratinous Material.

After mixing the two preparations (A) and (B), the ready-to-use mixture prepared in this way is applied to the keratinous material. In this context, it has proved particularly preferable to apply the mixture of (A) and (B) to the keratinous material directly after mixing, i.e., within a period of at most about 60 minutes, preferably at most about 45 minutes and most preferably at most about 30 minutes.

In the context of a further particularly preferred embodiment, a process as contemplated herein is therefore exemplified in that the mixture of (A) and (B) is applied to the keratinous material within a period of from about 1 to about 60 minutes, preferably from about 1 to about 45 minutes, and most preferably within a period of from about 1 to about 30 minutes after mixing thereof.

The application time during which the mixture of (A) and (B) acts on the keratinous material can in principle be from about 1 to about 60 minutes. However, a major advantage of the dyeing principle based on this system is that very intense and resistant dyeing's can be produced within very short periods of time. For this reason, it is particularly preferred to leave the application mixture prepared from (A) and (B) on the keratin material for a fairly short period of about 1 to about 10 minutes, and then to wash it out with water.

In the context of a further particularly preferred embodiment, a method as contemplated herein is therefore exemplified by (5) applying the mixture of (A) and (B) to the keratinous material, allowing the mixture to act on the keratinous material for a period of about 1 to about 10 minutes, and washing the mixture out with water.

Application of Further Compositions in the Procedure

In one embodiment, only the mixture of the two compositions (A) and (B) can be used on the keratinous material. However, when using the process of the present disclosure for dyeing keratinous material, it may also be particularly preferred if not only the two compositions (A) and (B), but furthermore at least one third composition (C) is applied to the keratinous material.

For example, this third composition (C) can be applied to the keratinous material after applying the mixture to (A) and (B).

Particularly preferably, the third composition (C) is applied to the keratin material after the mixture of (A) and (B) has been applied, allowed to act and rinsed out again with water. Within this embodiment, the third composition (C) may for example perform the function of a color sealant.

The color seal can be achieved by the composition (C) comprising at least one film-forming polymer.

In the context of a further particularly preferred embodiment, a method as contemplated herein comprising the (6) Applying a composition (C) to the keratinous material, wherein the composition (C) comprises:

(C1) at least one film-forming polymer.

Film-Forming Polymers

The composition (C) described above contains at least one film-forming polymer (C1).

However, as an optional additional ingredient, compositions (A) and (B) may also contain at least one film-forming polymer.

Polymers are macromolecules with a molecular weight of at least about 1000 g/mol, preferably of at least about 2500 g/mol, particularly preferably of at least about 5000 g/mol, which are formed of identical, repeating organic units. The polymers of the present disclosure may be synthetically produced polymers which are manufactured by polymerization of one type of monomer or by polymerization of different types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than about $10^7$ g/mol, preferably not more than about $10^6$ g/mol and particularly preferably not more than about $10^5$ g/mol.

As contemplated herein, a film-forming polymer is a polymer which can form a film on a substrate, for example on a keratinic material or a keratinic fiber. The formation of a film can be demonstrated, for example, by looking at the keratin material treated with the polymer under a microscope.

The film-forming polymers can be hydrophilic or hydrophobic.

In a first embodiment, it may be preferred to use at least one hydrophobic film-forming polymer in preparation (B), (C) and/or (D), most particularly in preparation (D).

A hydrophobic polymer is a polymer that has a solubility in water at 25° C. (760 mmHg) of less than about 1% by weight.

The water solubility of the film-forming, hydrophobic polymer can be determined in the following way, for example. 1.0 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, an agent as contemplated herein is exemplified in that it contains at least one film-forming hydrophobic polymer (c) selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth)acrylate; isononoyl(meth)acrylate; 2-ethylhexyl (meth)acrylate; lauryl (meth)acrylate; isopentyl (meth)acrylate; n-butyl (meth)acrylate); isobutyl (meth)acrylate; ethyl (meth)acrylate; methyl (meth)acrylate; tert-butyl (meth)acrylate; stearyl (meth)acrylate; hydroxyethyl (meth)acrylate; 2-hydroxypropyl (meth)acrylate; 3-hydroxypropyl (meth)acrylate and/or mixtures thereof.

Other film-forming hydrophobic polymers may be selected from the homo- or copolymers of (meth)acrylamide; N-alkyl-(meth)acrylamides, in those with C2-C18 alkyl groups, such as N-ethyl-acrylamide, N-tert-butyl-acrylamide, N-octyl-acrylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex® OPT (Acrylates/C12-22 Alkyl methacrylate Copolymer).

The homo- and copolymers of N-vinylpyrrolidone, vinyl-caprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF® under the trade name "Luvitol HSB".

It was also possible to obtain intensive and true-to-wash dyeing's when the composition (C) contained at least one film-forming polymer chosen from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process as contemplated herein is exemplified in that the composition (C) comprises at least one film-forming polymer which is selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may also be preferred to use at least one hydrophilic film-forming polymer in the composition (C).

A hydrophilic polymer is a polymer that has a solubility in water at 25° C. (760 mmHg) of more than about 1% by weight, preferably more than about 2% by weight.

The water solubility of the film-forming, hydrophilic polymer can be determined in the following way, for example. 1.0 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears microscopically homogeneous. If the polymer-water mixture cannot be assessed visually due to a high turbidity of the mixture, the mixture is filtered. If no undissolved polymer remains on the filter paper, the solubility of the polymer is more than 1% by weight.

Nonionic, anionic and cationic polymers can be used as film-forming, hydrophilic polymers.

Suitable film-forming hydrophilic polymers can be selected, for example, from the group of polyvinylpyrrolidone (co)polymers, polyvinyl alcohol (co)polymers, vinyl acetate (co)polymers, carboxyvinyl(co)polymers, acrylic acid (co)polymers, methacrylic acid (co)polymers, natural gums, polysaccharides and/or acrylamide (co)polymers.

Furthermore, it is particularly preferred to use polyvinylpyrrolidone (PVP) and/or a vinylpyrrolidone-containing copolymer as film-forming hydrophilic polymer.

In another particularly preferred embodiment, an agent as contemplated herein is exemplified in that it contains (c) at least one film-forming, hydrophilic polymer selected from the group of polyvinylpyrrolidone (PVP) and the copolymers of polyvinylpyrrolidone.

It is further preferred if the agent as contemplated herein contains polyvinylpyrrolidone (PVP) as the film-forming hydrophilic polymer. Surprisingly, the wash fastness of the dyeing's obtained with agents containing PVP (b) was also very good.

Particularly well-suited polyvinylpyrrolidones are available, for example, under the name Luviskol® K from BASF® SE, especially Luviskol® K 90 or Luviskol® K 85 from BASF® SE.

The polymer PVP K30, which is marketed by Ashland (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF®.

The use of film-forming hydrophilic polymers from the group of copolymers of polyvinylpyrrolidone has also led to particularly good and washfast color results.

Vinylpyrrolidone-vinyl ester copolymers, such as those marketed under the trademark Luviskol® (BASF®), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF® SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-containing copolymer.

Other suitable copolymers of polyvinylpyrrolidone may also be those obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In another very particularly preferred embodiment, an agent as contemplated herein is exemplified in that it comprises at least one film-forming, hydrophilic polymer selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another fussy copolymer of vinylpyrrolidone is the polymer known under the INCI designation maltodextrin/VP copolymer.

Furthermore, intensively dyed keratin material, especially hair, with very good wash fastness could be obtained if a non-ionic, film-forming, hydrophilic polymer was used as the film-forming, hydrophilic polymer.

In a first embodiment, it may be preferred if the composition (C) comprises at least one nonionic, film-forming, hydrophilic polymer.

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products containing, as anon-ionic, film-forming, hydrophilic polymer, at least one polymer selected from the group of
Polyvinylpyrrolidone,
Copolymers of N-vinylpyrrolidone and vinyl esters of carboxylic acids having 2 to 18 carbon atoms of N-vinylpyrrolidone and vinyl acetate,
Copolymers of N-vinylpyrrolidone and N-vinylimidazole and methacrylamide,
Copolymers of N-vinylpyrrolidone and N-vinylimidazole and acrylamide,
Copolymers of N-vinylpyrrolidone with N,N-di(C1 to C4)-alkylamino-(C2 to C4)-alkylacrylamide, If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from about 20:80 to about 80:20, in particular from about 30:70 to about 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF® SE.

Another particularly preferred polymer is selected from the INCI designation VP/Methacrylamide/Vinyl Imidazole Copolymer, which is available under the trade name Luviset® Clear from BASF® SE.

Another particularly preferred non-ionic, film-forming, hydrophilic polymer is a copolymer of N-vinylpyrrolidone and N,N-dimethylaminiopropylmethacrylamide, which is sold under the INCI designation VP/DMAPA Acrylates Copolymer e.g., under the trade name Styleze® CC 10 by ISP.

A cationic polymer of interest is the copolymer of N-vinylpyrrolidone, N-vinylcaprolactam, N-(3-dimethylaminopropyl)methacrylamide and 3-(methacryloylamino)propyl-lauryl-dimethylammonium chloride (INCI designation):

Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include
Vinylpyrrolidone-vinylimidazolium methochloride copolymers, as offered under the designations Luviquat® FC 370, FC 550 and the INCI designation Polyquaternium-16 as well as FC 905 and HM 552,
Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF® SE or Gafquat® 440, Gafquat® 734, Gafquat® 755 or Gafquat® 755N from Ashland Inc.

Polyquaternium-46 is the reaction product of vinylcaprolactam and vinylpyrrolidone with methylvinylimidazolium methosulfate and is available for example under the name Luviquat® Hold from BASF® SE. Polyquaternium-46 is preferably used in an amount of 1 to 5% by weight—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol® or under the names Synthalen® M and Synthalen® K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers which are produced from monomers of (methyl)acrylamido-C1-C4-alkyl sulphonic acid or the salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of the poly(meth)arylamido-$C_1$-$C_4$-alkyl sulphonic acids are cross-linked and at least about 90% neutralized. These polymers can or cannot be cross-linked.

Cross-linked and fully or partially neutralized polymers of the poly-2-acrylamido-2-methylpropane sulfonic acid type are available under the INCI designation "Ammonium Polyacrylamido-2-methyl-propanesulphonates" or "Ammonium Poly acryldimethyltauramides".

Another preferred polymer of this type is the cross-linked poly-2-acrylamido-2-methyl-propanesulphonic acid polymer marketed by Clamant under the trade name Hostacerin AMPS, which is partially neutralized with ammonia.

In another explicitly quite particularly preferred embodiment, a process as contemplated herein is exemplified in that the composition (C) comprises at least one anionic, film-forming, polymer.

In this context, the best results were obtained when the composition (C) contains at least one film-forming polymer comprising at least one structural unit of formula (P-I) and at least one structural unit of formula (P-II)

where
M is a hydrogen atom or ammonium (NH4), sodium, potassium, ½ magnesium or ½ calcium.

In a further preferred embodiment, a process as contemplated herein is exemplified in that the composition (C) comprises at least one film-forming polymer comprising at least one structural unit of the formula (P-I) and at least one structural unit of the formula (P-II)

where
M is a hydrogen atom or ammonium (NH4), sodium, potassium, ½ magnesium or ½ calcium.

When M represents a hydrogen atom, the structural unit of the formula (P-I) is based on an acrylic acid unit.
When M stands for an ammonium counterion, the structural unit of the formula (P-I) is based on the ammonium salt of acrylic acid.
When M stands for a sodium counterion, the structural unit of the formula (P-I) is based on the sodium salt of acrylic acid.
When M stands for a potassium counterion, the structural unit of the formula (P-I) is based on the potassium salt of acrylic acid.
If M stands for a half equivalent of a magnesium counterion, the structural unit of the formula (P-I) is based on the magnesium salt of acrylic acid.
If M stands for a half equivalent of a calcium counterion, the structural unit of the formula (P-I) is based on the calcium salt of acrylic acid.

The film-forming polymer(s) as contemplated herein are preferably used in certain ranges of amounts in the preparation (C) as contemplated herein. In this context, it has proved particularly preferable for solving the problem as contemplated herein if the preparation contains—in each case based on its total weight—one or more film-forming polymers in a total amount of from about 0.1 to about 18.0% by weight, preferably from about 1.0 to about 16.0% by weight, more preferably from about 5.0 to about 14.5% by weight and very particularly preferably from about 8.0 to about 12.0% by weight.

In a further preferred embodiment, a process as contemplated herein is exemplified in that the composition (C)- based on the total weight of the composition (C)-contains one or more film-forming polymers in a total amount of from about 0.1 to about 18.0% by weight, preferably from about 1.0 to about 16.0% by weight, more preferably from about 5.0 to about 14.5% by weight, and most preferably from about 8.0 to about 12.0% by weight.

Sequence of the Process Steps

It is typical of the method as contemplated herein that it comprises the steps (1), (2), (3), (4), (5). The process may further comprise the optional step (6).

Step (1) is directed to the preparation of composition (A), and step (2) is directed to the preparation of composition (B). These two steps can take place either simultaneously or successively, i.e., it is both as contemplated herein if step (1) takes place before step (2), if step (2) takes place before step (1) or if both steps (1) and (2) take place simultaneously.

In this context, it has been found preferable to carry out the preparation of the two compositions in step (3) depending on their respective planned storage times. For example, if Composition (A) is to be stored for a period of 10 days and Composition (B) is to be stored for a period of about 2 days, it is preferred to prepare composition (B) first and then composition (A). However, if the storage of composition (B) is to last for a period of about 10 days, while the storage of composition (A) is to last for a period of only about 5 days, then composition (A) is conveniently prepared before composition (B) in terms of time.

Following steps (1) and (2), respectively, the storage of the respective composition takes place with step (3). After storage of the compositions (A) and (B), they are mixed, i.e., step (4) of the process necessarily follows step (3). The mixture of (A) and (B) is applied to the keratin material, so that step (5) of the process also necessarily follows step (4).

Preference is therefore given to a method for the preparation and use of an agent for coloring keratinous material, in particular human hair, comprising the following steps: (1) Preparation of a first composition (A) comprising
(A1) less than about 10% by weight of water and
  (A2) one or more organic $C_1$-$C_6$ alkoxy silanes and/or condensation products thereof, and
(2) Preparation of a second composition (B) containing
  (B1) Water and
  (B2) one or more fat components and
  (B3) one or more colorant compounds selected from the group of pigments and/or direct dyes,
(3) Storage of the composition (A) and/or (B) for a period of at least about 24 hours,
(4) mixing compositions (A) and (B),
(5) applying the mixture of (A) and (B) to the keratinous material, wherein.
  Step (3) takes place after step (1), and
  Step (3) takes place after step (2), and
  Step (4) takes place after step (3), and
  Step (5) takes place after step (4).

The optionally feasible step (6) (i.e., the application of the composition (C)) is particularly preferably carried out in time after step (5).

Ready to Use Agent

By mixing compositions (A) and (B), a ready-to-use staining agent is prepared, which enables the intensive staining of keratinous material with very good fastness properties.

A second object of the present disclosure is therefore a ready-to-use agent for dyeing keratinous material, which has been prepared according to the process steps (1) to (4) as already disclosed in detail in the description of the first object of the present disclosure.

In other words, a second object of the present disclosure is therefore a ready-to-use agent for dyeing keratinous material obtainable by
(1) Preparation of a first composition (A) comprising
  (A1) less than about 10% by weight of water and
  (A2) one or more organic $C_1$-$C_6$ alkoxy silanes and/or condensation products thereof, and
(2) Preparation of a second composition (B) containing
  (B1) Water and
  (B2) one or more fat components and
  (B3) one or more colorant compounds selected from the group of pigments and/or direct dyes, and the
(3) Storing the composition (A) and/or (B) for a period of at least about 24 hours; and
(4) Mixing the compositions (A) and (B).

Regarding the further preferred embodiments of the composition ready for use as contemplated herein, mutatis mutantis what has been said about the method as contemplated herein applies.

Multi-Component Packaging Unit (Kit-of-Parts)

To increase user convenience, all preparations required for the application process, for the dyeing process, are provided to the user in the form of a multi-component packaging unit (kit-of-parts).

A second object of the present disclosure is a multi-component packaging unit (kit-of-parts) for treating keratinous material, comprising separately prepared
a first container comprising a first composition (A) and
a second container comprising a second composition (B), wherein
wherein the compositions (A) and (B) have already been disclosed in detail in the description of the first subject matter of the present disclosure.

Furthermore, the multi-component packaging unit as contemplated herein may also comprise a third packaging unit containing a cosmetic composition (C). Composition (C), as previously described, very particularly preferably contains at least one film-forming polymer colorant compound.

In a very particularly preferred embodiment, the multi-component packaging unit (kit-of-parts) as contemplated herein comprises, separately assembled from one another
a third container comprising a third composition (C), wherein the third composition (C) comprises at least one film-forming polymer.

With respect to the other preferred embodiments of the multi-component packaging unit as contemplated herein, the same applies mutatis mutandis to the procedure as contemplated herein.

EXAMPLES

1. Preparation of the Silane Blend (Composition (A))

A reactor with a heatable/coolable outer shell and with a capacity of 10 liters was filled with 4.67 kg of methyltrimethoxysilane (34.283 mol). With stirring, 1.33 kg of (3-aminopropyl)triethoxysilane (6.008 mol) was then added. This mixture was stirred at 30° C. Subsequently, 670 ml of distilled water (37.18 mol) was added dropwise with vigorous stirring while maintaining the temperature of the reaction mixture at 30° C. under external cooling. After completion of the water addition, stirring was continued for another 10 minutes. A vacuum of 280 mbar was then applied, and the reaction mixture was heated to a temperature of 44° C. Once the reaction mixture reached the temperature of 44° C., the ethanol and methanol released during the reaction were distilled off over a period of 190 minutes. During distillation, the vacuum was lowered to 200 mbar. The distilled alcohols were collected in a chilled receiver. The reaction mixture was then allowed to cool to room temperature. To the mixture thus obtained, 3.33 kg of hexamethyldisiloxane was then dropped while stirring. It was stirred for 10 minutes. In each case, 100 ml of the silane blend was filled into a bottle with a capacity of 100 ml and screw cap closure with seal. After filling, the bottles were tightly closed. The water content was less than 2.0% by weight.

2. Preparation of the Composition (B)

The following compositions (B) were prepared (unless otherwise indicated, all FIGURES are in wt. %).

Composition (B)

|  | B Gel | B Emulsion |
|---|---|---|
| Hydroxyethylcellulose | 1.0 | — |
| Cetyl alcohol ($C_{16}$ fatty alcohol) | — | 4.0 |
| Lorol techn. (C12-C18 fatty alcohols) | — | 4.0 |
| Ceteareth-30 (Cetearyl alcohol, ethoxylated 30 EO) | — | 2.0 |
| Lavanya Zuni (Neelikon Red) CI = 12490 | 0.3 | 0.3 |
| Lavanya Belmont CI = 74160 | 0.1 | 0.1 |
| Lavanya Revolutum (Neelikon Yellow) CI = 11680 | 0.8 | 0.6 |
| Water (dist.) | ad 100 | ad 100 |

Emulsion: All fat components were heated to 80° C. The water was also heated to 80° C. in a separate container. While stirring, the water was then slowly added to the fat phase. During cooling, the surfactant and pigments were added while stirring. The composition (B) was then allowed to cool to room temperature, and 200 g of each was poured into a bottle.

3. Preparation of the Compositions (C)

The following compositions were prepared (unless otherwise stated, all FIGURES are in wt. %).

|  | wt.-% |
|---|---|
| Ethylene/Sodium Acrylate Copolymer (25% solution) | 40.0 |
| Water | ad 100 |

3. Storage

The silane blend prepared and bottled in step 1 (composition (A)) was stored at 20° C. for a period of 21 days.

The compositions (B) prepared in step 2 were stored under defined conditions:

Storage (L)

| Comparison B-V1 Gel, stored | B-V2 Emulsion, not stored | B-E1 Emulsion, stored |
|---|---|---|
| Gel | Emulsion | Emulsion |
| 48 hours (2 days) | Coloring without storage | 48 hours (2 days) |
| 20° C. | — | 20° C. |

5. Application

The ready-to-use composition was prepared by mixing 1.5 g of composition (A) and 20 g of composition (B), respectively. Compositions (A) and (B) were each shaken for 1 minute. Then this ready-to-use agent was dyed on two strands of hair each (Kerling, Euronatural hair white).

One minute after completion of shaking, the ready-to-use composition was applied to a first strand (strand 1), left to act for 1 min, and then rinsed out. 25 min after completion of shaking, the ready-to-use composition was applied to a second strand (strand 2), left to act for 1 min and then rinsed out.

Subsequently, the composition (C) was applied to each hair strand, left to act for 5 minutes and then also rinsed with water.

The two dyed strands were each dried and visually compared under a daylight lamp.

Afterwards, the strands were washed 5 times by hand with the aid of a shampoo (Schauma, 7-herbs) (5 hair washes=5 HW), dried and compared again visually under a daylight lamp.

|  | Comparison V1 | Comparison V2 | Disclosure E1 |
|---|---|---|---|
| Composition (A) | Silane blend (A) Storage 21 days, 20° C. | Silane blend (A) Storage 21 days, 20° C. | Silane blend (A) Storage 21 days, 20° C. |
| Composition (B) | B-V1 Gel, Storage 2 days, 20° C. | B-V2 Emulsion, no storage | B-E1, Emulsion Storage 2 days, 20° C. |
| Mixture (A) + (B) | 1.5 g (A) + 20.0 g (B-V1) | 1.5 g (A) + 20.0 g (B-V2) | 1.5 g (A) + 20.0 g (B-E1) |
| Composition (C) | 10.0 g (C) | 10.0 g (C) | 10.0 g (C) |
| Color difference between strand 1 and 2 | high | low | low |
| Color difference strand 1 before and after 5 HW | low | high | low |
| Color difference strand 2 before and after 5 HW | low | high | low |
| Color difference between strand 1 and 2 after 5 HW | high | high | low |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for the preparation and use of an agent for coloring keratinous material, comprising the following steps:

(1) preparing a first composition (A) comprising (A1) less than about 10% by weight of water and (A2) one or more organic C1-C6 alkoxy silanes and/or condensation products thereof, and (2) preparing a second composition (B) comprising (B1) water (B2) one or more fat components and (B3) one or more colorant compounds selected from the group of pigments and/or direct dyes, (3) storing the composition (A) and/or (B) for a period of at least about 24 hours,
(4) mixing compositions (A) and (B),
(5) applying the mixture of (A) and (B) on the keratinic material.

2. The method according to claim 1, wherein the first composition (A) comprises—based on a total weight of the composition (A)—about 0.01 to about 9.5% by weight of the water (A1).

3. The method according to claim 1, wherein the one or more organic C1-C6 alkoxy silanes (A2) comprise the one or more organic C1-C6 alkoxy silanes of formula (S-I) and/or (S-II), $$R_1R_2N\text{-}L\text{-}Si(OR_3)_a(R_4)_b \quad (S\text{-}I)$$

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a, stands for an integer from 1 to 3, and
b stands for the integer 3-a, and $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (S\text{-}II),$$

where
R5, R5', R5'', R6, R6' and R6'' independently represent a $C_1$-$C_6$ alkyl group,
A, A', A'', A''' and A'''' independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III), $$(A'''')\text{-}Si(R_6'')_{d''}(OR_5'')_{c''} \quad (S\text{-}III),$$

where
c, stands for an integer from 1 to 3,
d stands for the integer 3-c,
c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
provided that at least one of e, f, g and h is different from 0,
and/or their condensation products.

4. The method according to claim 3, wherein the at least one $C_1$-$C_6$ organic alkoxysilane (A2) of formula (S-I) is selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane,
(2-Dimethylaminoethyl)trimethoxysilane
and/or their condensation products.

5. The method according to claim 3, wherein the one or more organic $C_1$-$C_6$ alkoxy silanes (A2) comprises a compound of formula (S-IV), $$R_9Si(OR_{10})_k(R_{11})_m \quad (S\text{-}IV),$$

where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group
k is an integer from 1 to 3, and
m stands for the integer 3-k,
and/or their condensation products.

6. The method according to claim 3, wherein the at least one $C_1$-$C_6$ organic alkoxysilane (A2) comprises a compound of formula (S-IV) selected from the group of
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
and/or their condensation products.

7. The method according to claim 1, wherein the first composition (A) comprises—based on a total weight of the composition (A)—the one or more organic $C_1$-$C_6$-alkoxysilanes (A2) and/or the condensation products thereof in a total amount of about 30.0 to about 85.0 wt. %.

8. The method according to claim 1, wherein the first composition (A) comprises at least one cosmetic ingredient selected from the group of hexamethyldisiloxane, octamethyltrisiloxane, decamethyltetrasiloxane, hexamethylcyclotrisiloxane, octamethylcyclotetrasiloxane, decamethylcyclopentasiloxane, and combinations thereof.

9. The method according to claim 1, wherein the first composition (A) comprises —based on the total weight of the composition (A) —about 10.0 to about 50.0% by weight of hexamethyldisiloxane.

10. The method according to claim 1, wherein the second composition (B) comprises —based on a total weight of the composition (B) —about 10.0 to about 90.0% by weight of the water (B1).

11. The method according to claim 1, wherein the one or more fat components (B2) comprises a compound selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

12. The method according to claim 1, wherein the one or more fat components (B2) comprise one or more $C_{12}$-$C_{30}$ fatty alcohols selected from the group of dodecan-1-ol, tetradecan-1-ol, hexadecan-1-ol, octadecan-1-ol, eicosan-1-ol, heneicosan-1-ol, docosan-1-ol, (9Z)-octadec-9-en-1-ol, (9E)-Octadec-9-en-1-ol, (9Z,12Z)-Octadeca-9,12-dien-1-ol, (9Z,12Z,15Z)-Octadeca-9,12,15-trien-1-ol, (9Z)-Eicos-9-en-1-ol, (5Z,8Z,11Z,14Z)-Eicosa-5,8,11,14-tetraen-1-ol, (13Z)-docos-13-en- 1-ol), (13E)-docosen-1-ol), 2-octyl-dodecanol, 2-hexyl-dodecanol and/or 2-butyl-dodecanol.

13. The method according to claim 1, wherein the second composition (B) comprises—based on a total weight of the composition (B)—the one or more fat components (B2) in a total amount of from about 2.0 to about 50.0% by weight.

14. The method according to claim 1, wherein the second composition (B) comprises at least one nonionic surfactant of formula (T-I), $$Ra\text{-}[O\text{-}CH_2\text{-}CH_2]_n\text{-}OH \quad (T\text{-}1)$$

wherein
- Ra is a saturated or unsaturated, unbranched or branched $C_8$-$C_{24}$ alkyl group, and
- n is an integer from about 10 to about 40.

15. The method according to claim 1, wherein (3) storing the composition (A) comprises storing the composition (A) for a period of at least about 5 days.

16. The method according to claim 1, wherein mixing the compositions (A) and (B) comprises mixing the compositions (A) and (B) in a weight ratio (A)/(B) of from about 1:20 to about 20:1.

17. The method according to claim 1, wherein applying the mixture of (A) and (B) comprises applying the mixture of (A) and (B) to the keratinous material within a period of from about 1 to about 60 minutes after mixing.

18. The method according to claim 1, comprising the steps of (6) Applying a composition (C) to the keratinous material, wherein the composition (C) comprises:
(C1) at least one film-forming polymer.

19. A multicomponent packaging unit (kit-of-parts) for treating keratinous material, comprising
- a first container containing a first composition (A), where the first composition (A) comprises (A1) less than about 10% by weight of water and (A2) one or more organic $C_1$-$C_6$ alkoxy silanes and/or condensation products thereof, and
- a second container containing a second composition (B), wherein the second composition (B) comprises (B1) water, (B2) one or more fat components, and (B3) one or more colorant compounds selected from the group of pigments and/or direct dyes.

20. A kit-of-parts according to claim 19, further comprising s
- a third container comprising a third composition (C), wherein the third composition (C) comprises at least one film-forming polymer.

* * * * *

UNITED STATES PATENT AND TRADEMARK OFFICE
CERTIFICATE OF CORRECTION

PATENT NO.         : 11,737,967 B2
APPLICATION NO.    : 17/614049
DATED              : August 29, 2023
INVENTOR(S)        : Ulrike Schumacher et al.

Page 1 of 1

It is certified that error appears in the above-identified patent and that said Letters Patent is hereby corrected as shown below:

In the Specification

Column 7, Line 10 change "(S4)" to --(SI)--.
Column 7, Line 32 change "(OR$_5$")" to --(OR$_5$")$_c$"--.
Column 8, Line 5 change "(S4)" to --(SI)--.
Column 10, Line 66 change "[O-(A''')]$_g$" to --[O-(A")]$_g$--.
Column 11, Line 19 change "A, A', A", A''' and A''''" to --A, A', A", A''' and A''''--.
Column 11, Line 21 change "A, A', A", A' and A''''" to --A, A', A", A''' and A''''--.
Column 11, Line 23 change "A, A', A", A''' and A''''" to --A, A', A", A''' and A''''--.
Column 11, Line 27 change "A, A', A", A''' and A''''" to --A, A', A", A''' and A''''--.
Column 11, Line 29 change "A, A', A", A' and A''''" to --A, A', A", A''' and A''''--.
Column 11, Line 47 change "(OR$_5$)$_c$''''" to --(OR$_5$")$_c$''--.
Column 12, Line 44 change "(triethoxysilyl)propyl" to --(triethoxysilyl) propyl--.
Column 18, Line 10 change "  " to -- --.
Column 31, Line 1 change "R$_2$" to --R$^2$--.
Column 53, Line 56 change "poly(meth)arylamido-C$_1$-C$_4$-alkyl" to --poly(meth)arylamido-C1-C4-alkyl--.
Column 54, Line 19 change "NH4" to --NH$_4$--.
Column 54, Line 36 change "NH4" to --NH$_4$--.

In the Claims

Column 58, Line 60 change "C1-C6" to --C$_1$-C$_6$--.
Column 59, Line 11 change "C1-C6" to --C$_1$-C$_6$--.
Column 59, Line 12 change "C1-C6" to --C$_1$-C$_6$--.
Column 59, Line 60 change "(2-Dim ethylaminoethyl)triethoxysilane" to --(2-Dimethylaminoethyl)triethoxysilane--.

Signed and Sealed this
Twenty-first Day of November, 2023

Katherine Kelly Vidal
*Director of the United States Patent and Trademark Office*